US010207919B2

(12) United States Patent
Donnio et al.

(10) Patent No.: US 10,207,919 B2
(45) Date of Patent: Feb. 19, 2019

(54) HYBRID NANOPARTICLES CONTAINING DENDRONS, METHODS OF PRODUCING SUCH HYBRID NANOPARTICLES, AND USES THEREOF

(71) Applicants: RHODIA OPERATIONS, Paris (FR); THE TRUSTEES OF THE UNIVERSITY OF PENNSYLVANIA, Philadelphia, PA (US); CENTRE NATIONAL DE LA RECHERCHE SCIENTIFIQUE, Paris (FR)

(72) Inventors: Bertrand Donnio, Strasbourg (FR); Davit Jishkariani, Philadelphia, PA (US); Benjamin Diroll, Philadelphia, PA (US); Lawrence Alan Hough, Seoul (KR); Christopher Murray, Bala Cynwyd Lower Merion, PA (US); Matteo Cargnello, Palo Alto, CA (US); Ludivine Malassis, Philadelphia, PA (US)

(73) Assignees: Rhodia Operations, Paris (FR); Centre National De La Recherche Scientifique, Paris (FR); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/580,905

(22) PCT Filed: Jun. 10, 2016

(86) PCT No.: PCT/US2016/037000
§ 371 (c)(1),
(2) Date: Dec. 8, 2017

(87) PCT Pub. No.: WO2016/201310
PCT Pub. Date: Dec. 15, 2016

(65) Prior Publication Data
US 2018/0162726 A1  Jun. 14, 2018

Related U.S. Application Data

(60) Provisional application No. 62/174,670, filed on Jun. 12, 2015, provisional application No. 62/311,504, filed on Mar. 22, 2016.

(51) Int. Cl.
| | |
|---|---|
| B82B 1/00 | (2006.01) |
| B82B 3/00 | (2006.01) |
| C07F 1/12 | (2006.01) |
| C09D 7/20 | (2018.01) |
| C09D 7/40 | (2018.01) |
| B82Y 30/00 | (2011.01) |
| C09C 1/62 | (2006.01) |
| B82Y 40/00 | (2011.01) |

(52) U.S. Cl.
CPC ........... *B82B 1/008* (2013.01); *B82B 1/00* (2013.01); *B82B 3/00* (2013.01); *B82B 3/0095* (2013.01); *C07F 1/12* (2013.01); *C09D 7/20* (2018.01); *C09D 7/67* (2018.01); *B82Y 30/00* (2013.01); *B82Y 40/00* (2013.01); *C01P 2002/86* (2013.01); *C01P 2002/88* (2013.01); *C01P 2004/04* (2013.01); *C01P 2004/64* (2013.01); *C09C 1/62* (2013.01); *Y10S 977/773* (2013.01); *Y10S 977/81* (2013.01); *Y10S 977/892* (2013.01); *Y10S 977/896* (2013.01)

(58) Field of Classification Search
CPC ......... B82B 1/008; B82B 3/0095; C09D 7/20; C09D 7/67; B82Y 30/00; B82Y 40/00; Y10S 977/773; Y10S 977/81; Y10S 977/892; Y10S 977/896
USPC ........................................................ 428/403
See application file for complete search history.

(56) References Cited

U.S. PATENT DOCUMENTS

| | | | |
|---|---|---|---|
| 7,253,004 B2 | 8/2007 | Vossmeyer et al. | |
| 7,273,904 B2 | 9/2007 | Peng et al. | |
| 7,297,298 B2 | 11/2007 | Matsunami et al. | |
| 2002/0068795 A1 | 6/2002 | Won et al. | |
| 2002/0123609 A1 | 9/2002 | Frechet et al. | |
| 2004/0101976 A1 | 5/2004 | Peng et al. | |
| 2004/0166166 A1 | 8/2004 | Matsunami et al. | |
| 2005/0004293 A1 | 1/2005 | Peng et al. | |
| 2006/0177376 A1 | 8/2006 | Tomalia et al. | |
| 2006/0219159 A1 | 10/2006 | Rakow et al. | |
| 2008/0152911 A1 | 6/2008 | Wendland et al. | |
| 2009/0182151 A1 | 7/2009 | Wu et al. | |
| 2009/0203196 A1 | 8/2009 | Kim et al. | |
| 2010/0001235 A1 | 1/2010 | Newkome et al. | |
| 2011/0065896 A1 | 3/2011 | Licha et al. | |
| 2011/0207868 A1 | 8/2011 | Wendland et al. | |

(Continued)

FOREIGN PATENT DOCUMENTS

| | | |
|---|---|---|
| WO | 98/30604 A1 | 7/1998 |
| WO | 2010/030252 A2 | 3/2010 |

OTHER PUBLICATIONS

Oberg, K. et al., Langmuir, 2012, vol. 29, No. 1, pp. 456-465.*

(Continued)

*Primary Examiner* — Leszek B Kiliman

(57) ABSTRACT

The present disclosure relates to a hybrid nanoparticle comprising a metallic core and at least one lipophilic dendron attached to the surface of the metallic core, and methods of producing such hybrid nanoparticles. The present disclosure also relates to films containing the hybrid nanoparticles described herein.

19 Claims, 15 Drawing Sheets

(56) References Cited

U.S. PATENT DOCUMENTS

2012/0029062 A1     2/2012    Gunaratne et al.
2014/0128451 A1     5/2014    Gunaratne et al.

OTHER PUBLICATIONS

Danda, C. et al., Macromolecular Chemistry and Physics, 2011, vol. 212, No. 15, pp. 1600-1615.*

Oberg, K. et al., "Templating gold surfaces with function: A self-assembled dendritic monolayer methodology based on monodisperse polyester scaffolds," Langmuir, 2012, vol. 29, No. 1, pp. 456-465.

Danda, C. et al., "Gold nanoparticle/carbazole dendron hybrids," Macromolecular Chemistry and Physics, 2011, vol. 212, No. 15, pp. 1600-1615.

Ostmark, E. et al., "Dendritic structures based on bis (hydroxymethyl) propionic acid as platforms for surface reaction," Langmuir, 2005, vol. 21, No. 10, pp. 4512-4519.

Lundgren, A. et al., "Self-assembled arrays of dendrimer-gold-nanoparticle hybrids for functional cell studies," Angewandte Chemie International Edition, 2011, vol. 50, No. 15, pp. 3450-3453.

Jishkariani, D. et al., "Dendron-mediated engineering of interparticle separation and self-assembly in dendronized gold nanoparticles super lattices," Journal of the American Chemical Society, Aug. 10, 2015, vol. 137, No. 33, pp. 10728-10734.

Chen, Z. et al., "Binary Nanoparticle Superlattices in the Semiconductor—Semiconductor System: CdTe and CdSe," Journal of the American Chemical Society, 2007, vol. 129, No. 50, pp. 15702-15709.

Donnio, B., et al., "Dendronized Ferromagnetic Gold Nanoparticles Self-Organized in a Thermotropic Cubic Phase," Advanced Materials, 2007, vol. 19, pp. 3534-3539.

Rodriguez-Fernandez, J., et al., "Seeded Growth of Submicron Au Colloids with Quadrupole Plasmon Resonance Modes," Langmuir, 2006, vol. 22, No. 16, pp. 7007-7010.

Gillies, E.R., et al., "Designing Macromolecules for Therapeutic Applications: Polyester Dendrimer-Poly(ethylene oxide) "Bow-Tie" Hybrids with Tunable Molecular Weight and Architecture," Journal of the American Chemical Society, 2002, vol. 124, No. 47, pp. 14137-14146.

Ihre, H., et al., "Double-Stage Convergent Approach for the Synthesis of Functionalized Dendritic Aliphatic Polyesters Based on 2, 2-Bis(hydroxymethyl)propionic Acid," Macromolecules, 1998, vol. 31, No. 13, pp. 4061-4068.

Jain, P.K., et al., "On the Universal Scaling Behavior of the Distance Decay of Plasmon Coupling in Metal Nanoparticle Pairs: A Plasmon Ruler Equation," Nano Letters, 2007, vol. 7, No. 7, pp. 2080-2088.

Kanie, K., et al., "Simple Cubic Packing of God Nanoparticles through Rational Design of Their Dendrimeric Corona," Journal of the American Chemical Society, 2012, vol. 134, pp. 808-811.

Marcos, M., et al., "Dendromesogens: Liquid Crystal Organizations of Poly(amidoamine) Dendrimers versus Starburst Structures," Chemistry—A European Journal, 2001, vol. 7, No. 5, pp. 1006-1013.

Mischler, S., et al., "Design of liquid-crystalline gold nanoparticles by click chemistry," ChemComm, 2012, vol. 48, pp. 2183-2185.

Peng, S., et al., "A Facile Synthesis of Monodisperse Au Nanoparticles and Their Catalysis of CO Oxidation," Nano Research, 2008, vol. 1, pp. 229-234.

Reinhard, B.M., et al., "Calibration of Dynamic Molecular Rulers Based on Plasmon Coupling between Gold Nanoparticles," Nano Letters, 2005, vol. 5, No. 11, pp. 2246-2252.

Srivastava, S., et al., "Controlled Plasmon Resonance of Gold Nanoparticles Self-Assembled with PAMAM Dendrimers," Chem. Mater., 2005, vol. 17, No. 3, pp. 487-490.

* cited by examiner

HYBRID NANOPARTICLES CONTAINING DENDRONS, METHODS OF PRODUCING SUCH HYBRID NANOPARTICLES, AND USES THEREOF

CROSS REFERENCE TO RELATED APPLICATIONS

This application is a U.S. national phase entry under 35 U.S.C. § 371 of International Application No. PCT/US2016/037000, filed on Jun. 10, 2016, which claims the priority of U.S. Provisional Application Nos. 62/174,670 filed Jun. 12, 2015 and 62/311,504 filed Mar. 22, 2016. The entire contents of these applications are explicitly incorporated herein by this reference for all purposes.

FIELD OF THE INVENTION

The present disclosure relates to a hybrid nanoparticle comprising a metallic core and at least one lipophilic dendron attached to the surface of the metallic core, and methods of producing such hybrid nanoparticles. The present disclosure also relates to films containing the hybrid nanoparticles described herein and their use, for example, in solid-state devices, such as optical, magnetic and electronic devices.

BACKGROUND

Although substantial efforts have been made to decrease interparticular spacings in NP solids, typically for enhanced conductivity, many optical phenomena such as plasmonic enhancement of photoluminescence have ideal interparticle separations greater than the 1-2 nm typically accessed with commercially available ligands, such as alkylthiols, ω-functionalized alkylthiols, etc. To date, lithographic methods have been used to study these effects, but recent approaches including DNA hybridization of NPs, liquid-crystals functionalization, liquid crystals defects and block copolymers surface templates, have been reported. Inter-particle spacings modulation in the range of 0.6-1.9 nm have been achieved in binary mixtures of poly(amidoamine) dendrimers (PAMAM, G0-G4) and mercaptoundecanoic acid passivated gold NPs prepared via co-precipitation, but without control of the ordering (see, for example, Srivastava, S.; Frankamp, B. L.; Rotello, V. M. *Chem. Mater.* 2005, 17, 487). In all cases, the distance modulation is presented in dimers, trimers, or in small particles clusters, and the accessible range is limited.

Studies of 2D arrays of iron oxide NPs, liquid-crystalline self-assemblies of dendronized gold nanoparticles (see, for example, Donnio, B.; Garcia-Vázquez, P.; Gallani, J. L.; Guillon, D.; Terazzi, E. *Adv. Mater.* 2007, 19, 3534; Kanie, K.; Matsubara, M.; Zeng, X.; Liu, F.; Ungar, G.; Nakamura, H.; Muramatsu, A. *J. Am. Chem. Soc.* 2012, 134, 808; and Mischler, S.; Guerra S.; Deschenaux. R. *Chem. Commun.* 2012, 48, 2183), construction of covalently bound dendrimer-NP multilayers, and the use of dendronized hybrid systems in drug delivery, imaging and theranostics, as well as recoverable catalysts, are also known.

Achieving interparticle distance control while still preserving ordered assemblies of NPs over large areas with high uniformity is an important and unresolved challenge that is inevitable for the fabrication of solid-state devices and metamaterials based on NPs. Herein, hybrid nanoparticles capable of interparticle distance control while still preserving ordered assemblies over large areas with high uniformity are described.

SUMMARY OF THE INVENTION

In a first aspect, the present disclosure relates to a hybrid nanoparticle comprising:
(a) a metallic core, and
(b) at least one dendron attached to the surface of the metallic core;
wherein the at least one dendron is a lipophilic dendron.

In a second aspect, the present disclosure relates to a film comprising a plurality of hybrid nanoparticles described herein.

In a third aspect, the present disclosure relates to a dendrimer represented by the structure

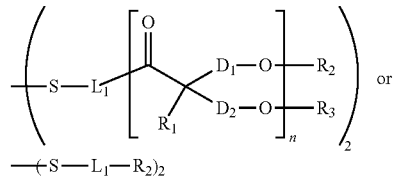

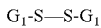

wherein
each occurrence of $R_1$ is H or $C_1$-$C_{20}$ alkyl,
each occurrence of $D_1$ and $D_2$ are each, independently, $C_1$-$C_{20}$ alkylene,
each occurrence of $L_1$ is $C_1$-$C_{20}$ alkylene,
each occurrence $R_2$ and $R_3$ are each, independently, H, $C_1$-$C_{38}$ alkyl, $C_2$-$C_{38}$ alkenyl, or $C_2$-$C_{38}$ alkynyl,
n is from 1 to 6;
wherein $R_1$, $D_1$, and $D_2$, $L_1$, $R_2$, and $R_3$, are each optionally interrupted by one or more divalent moieties.

In a fourth aspect, the present disclosure relates to a method for producing the dendrimer described herein, the method comprising:
reacting a compound represented by the structure $$G_1\text{-S—S-}G_1$$

with a compound represented by the structure

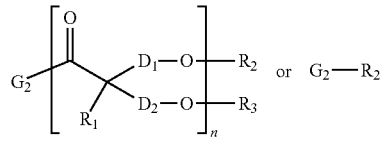

wherein
each occurrence of $R_1$ is H or $C_1$-$C_{20}$ alkyl,
each occurrence of $D_1$ and $D_2$ are each, independently, $C_1$-$C_{20}$ alkylene,
each occurrence $R_2$ and $R_3$ are each, independently, H, $C_1$-$C_{38}$ alkyl, $C_2$-$C_{38}$ alkenyl, or $C_2$-$C_{38}$ alkynyl,
n is from 1 to 6;
wherein $R_1$, $D_1$, and $D_2$, $R_2$, and $R_3$, are each optionally interrupted by one or more divalent moieties;
each occurrence of $G_1$ is a substituent comprising a reactive group capable of reacting with the reactive group in $G_2$, and $G_2$ is a substituent comprising a reactive group capable of reacting with the reactive group in $G_1$.

In a fifth aspect, the present disclosure relates to a method for producing the hybrid nanoparticle described herein, the method comprising:
(i) producing the dendrimer described herein, and
(ii) contacting the dendrimer produced in step (i) with a metallic nanoparticle; thereby producing the hybrid nanoparticle.

In a sixth aspect, the present disclosure relates to a composition comprising at least one hybrid nanoparticle described herein and a liquid carrier.

In a seventh aspect, the present disclosure relates to method for producing the film described herein, the method comprising:
(i) coating a composition described herein on the surface of a liquid immiscible with the liquid carrier of the composition, and
(ii) removing the liquid carrier of the composition, thereby producing the film.

In an eighth aspect, the present disclosure relates to a method for producing a ring structure comprising a plurality of the hybrid nanoparticles described herein, the method comprising:
(i) coating a composition described herein, the liquid carrier of which comprises a residual amount of water, on the surface of a support, and
(ii) removing the liquid carrier of the composition, thereby producing the ring structure.

An object of the present disclosure is to provide precise interparticle distance control while still preserving ordered assemblies of NPs over large areas with high uniformity.

Another object of the present disclosure is to provide monodisperse and homogeneous nanoparticle coatings that foster the formation of NP superlattices with a precise control over inter-particle distances in a range that is intermediate between commercial and DNA-based ligands.

BRIEF DESCRIPTION OF THE FIGURES

FIG. 8a is from a Au@G2 film, and FIG. 8b is from a Au@G4 film.

FIG. 12d shows a proposed scheme ring formation.

FIG. 13d shows a schematic of the transition from suspension to monolayers for inventive hybrid nanoparticles of different sizes.

DETAILED DESCRIPTION

Figure 1:
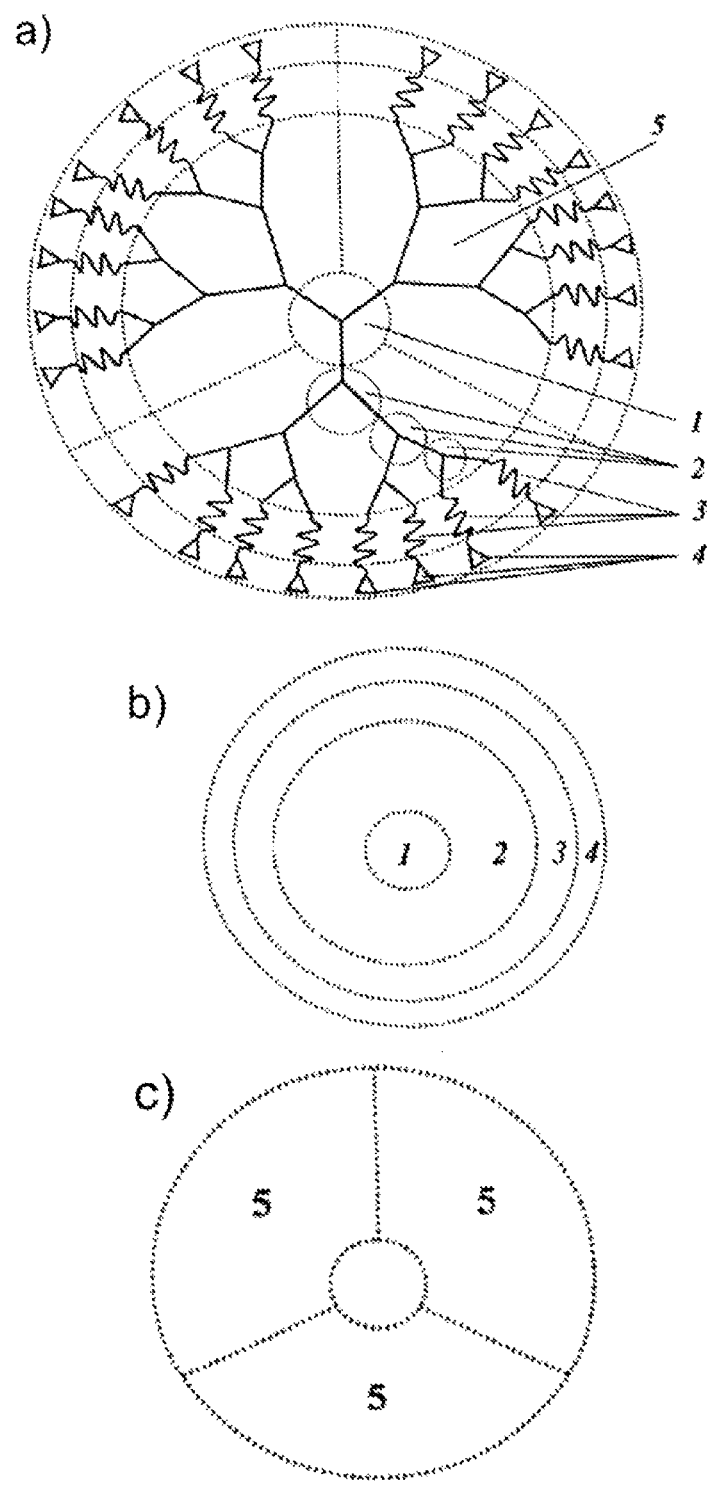
FIG. 1 schematically shows (a) the general structure of a dendrimer, (b) the spatial arrangement of four different units which make up a typical dendrimer, and (c) segments of dendrons in a typical dendrimer.

As used herein, the terms "a", "an", or "the" means "one or more" or "at least one" unless otherwise stated.

As used herein, the term "comprises" includes "consists essentially of" and "consists of." The term "comprising" includes "consisting essentially of" and "consisting of."

Throughout the present disclosure, various publications may be cited and/or may be incorporated by reference. Should the meaning of any language in such publications incorporated by reference conflict with the meaning of the language of the present disclosure, the meaning of the language of the present disclosure shall take precedence, unless otherwise indicated.

As used herein, the terminology "(Cx-Cy)" in reference to an organic group, wherein x and y are each integers, means that the group may contain from x carbon atoms to y carbon atoms per group.

As used herein, the term "alkyl" means a monovalent straight or branched saturated hydrocarbon radical, more typically, a monovalent straight or branched saturated ($C_1$-$C_{40}$) hydrocarbon radical, such as, for example, methyl, ethyl, n-propyl, isopropyl, n-butyl, isobutyl, tert-butyl, hexyl, 2-ethylhexyl, octyl, hexadecyl, octadecyl, eicosyl, behenyl, tricontyl, and tetracontyl.

As used herein, the term "alkenyl" means a monovalent straight or branched unsaturated hydrocarbon radical, more typically, a monovalent straight or branched unsaturated ($C_2$-$C_{40}$) hydrocarbon radical, having one or more double bonds. Double bonds may have E or Z configuration, based on IUPAC designation, and may be isolated or conjugated. Examples of alkenyl groups include, but are not limited to, ethenyl, n-butenyl, linoleyl, and oleyl.

As used herein, the term "alkynyl" means a monovalent straight or branched unsaturated hydrocarbon radical, more typically, a monovalent straight or branched unsaturated ($C_2$-$C_{40}$) hydrocarbon radical, having one or more triple bonds. Triple bonds may be isolated or conjugated. Examples of alkynyl groups include, but are not limited to, ethynyl, n-propynyl, and n-butynyl.

As used herein, the term "alkylene" means a divalent straight or branched saturated hydrocarbon radical, more typically, a divalent straight or branched saturated ($C_1$-$C_{40}$) hydrocarbon radical, such as, for example, methylene, ethylene, n-propylene, n-butylene, hexylene, 2-ethylhexylene, octylene, hexadecylene, and octadecylene.

Any substituent described herein may optionally be substituted at one or more carbon atoms with one or more, same or different, substituents described herein. For instance, an alkylene group may be further substituted with an alkyl group. Any substituent described herein may optionally be substituted at one or more carbon atoms with one or more substituents selected from the group consisting of halogen, such as, for example, F, Cl, Br, and I; nitro ($NO_2$), cyano (CN), amino ($NH_2$), carboxylic and benzoic acids ($CO_2H$, $PhCO_2H$) and hydroxy (OH).

The present disclosure relates to a hybrid nanoparticle comprising:
(a) a metallic core, and
(b) at least one dendron attached to the surface of the metallic core;
   wherein the at least one dendron is a lipophilic dendron.

The metallic core comprises or consists of a metal, or an alloy or intermetallic comprising a metal. Metals include, for example, main group metals such as, e.g., lead, tin, bismuth, antimony and indium, and transition metals, e.g., a transition metal selected from the group consisting of gold, silver, copper, nickel, cobalt, palladium, platinum, iridium, osmium, rhodium, ruthenium, rhenium, vanadium, chromium, manganese, niobium, molybdenum, tungsten, tantalum, titanium, zirconium, zinc, mercury, yttrium, iron and cadmium. The metallic core may comprise or consist of oxides of the metals described herein.

In an embodiment, the metallic core comprises a transition metal.

In an embodiment, the metallic core comprises gold.

The hybrid nanoparticle of the present disclosure comprises at least one dendron attached to the surface of the metallic core.

Dendritic polymers include generally any of the known dendritic architectures including dendrimers, dendrons, typically regular dendrons, controlled hyperbranched polymers, dendrigrafts, and random hyperbranched polymers. Dendritic polymers are polymers with densely branched structures having a large number of reactive groups. A dendritic polymer includes several layers, or generations, of repeating units which all contain one or more branch points. Dendritic polymers, including dendrimers and hyperbranched polymers, are prepared by condensation reactions of monomeric units having at least two reactive groups. In general, dendrimers comprise a plurality of dendrons that emanate from a common core, which can be a single atom or a group of atoms. Each dendron generally consists of terminal surface groups, interior branch junctures having branching functionalities greater than or equal to two, and divalent connectors that covalently connect neighboring branching junctures.

Dendrons and dendrimers can be prepared by convergent or divergent synthesis. Divergent synthesis of dendrons and dendrimers involves a molecular growth process which occurs through a consecutive series of geometrically progressive step-wise additions of branches upon branches in a radially outward molecular direction to produce an ordered arrangement of layered branched shells.

Convergent synthesis of dendrimers and dendrons involves a growth process which begins from what will become the surface of the dendron or dendrimer and progresses radially in a molecular direction toward a focal point or core. The dendritic polymers may be ideal or non-ideal, i.e., imperfect or defective. Imperfections are normally a consequence of either incomplete chemical reactions, or unavoidable competing side reactions.

The general structure of dendrimers is schematically shown in FIG. 1a. The center of the structure is the core 1, which is typically non-metallic. In the example of FIG. 1a the core has three arms, or dendrons. However, in general the core can have any number of dendrons. Herein, the term "dendron" refers to a dendritic arm that is attached to a core, which core may be non-metallic or metallic.

Each dendron of the core begins with a first "shell" of repeating units 2 connected, each of which branches into at least two new branches. When going from the core to the outside of the structure, the example shown in FIG. 1a comprises altogether three shells of repeating units. Therefore, the dendrimer structure shown is called a generation-3 (G3) dendrimer. According to the present disclosure, dendrimers and dendrons of various generations can be used. Typically, generations 1-6, still more typically, generations 1-4, are used. In the example shown in FIG. 1a, since each repeating unit shown branches into two limbs, each shell of repeating units is doubling the total number of branches. Therefore the whole number of branches at the surface of the structure is 24 ($3\times2^n$, wherein n is the generation). In general, it is also possible to have dendrimer structures in which each repeating unit branches into more than two limbs. When going from the inside to the outside of the structure shown in FIG. 1a, the last shell of repeating units is optionally followed by a shell of spacer units 3. As seen in the figure, to each of the 24 branches a spacer unit is connected. These optional spacer units have the function to bind the capping groups 4 to the outer shell of repeating units. Typically, the capping groups 4 are connected directly to the last shell of the repeating units.

FIG. 1b schematically shows the spatial arrangement of the four different units, which form a typical dendrimer structure. In center is the core 1, which is surrounded by at least one shell of repeating units 2. The shells of repeating units are followed by a shell of optional spacer units 3, which at the outside of the dendrimer is surrounded by an outer shell of capping groups 4. The shells of repeating units may be formed by chemically and structurally identical units or by chemically and/or structurally different units. The repeating units may be different from shell to shell and/or may differ within one shell. In addition, the dendrimer structure may comprise chemically and/or structurally identical or different capping groups and optional spacer units. The repeating units may be attached to the core through covalent bonds such as carbon-carbon bonds or functional bonds, for example, ester bonds, amide bonds, and thioether bonds.

According to the number of dendrons of the core 1, the dendrimer structure may be divided into dendrons 5 as shown in FIG. 1c. If the dendrimer is synthesized by a convergent approach, the chemical composition and/or the structural features of the dendrons (repeating units, the optional spacer units, and/or the capping groups) may differ from dendron to dendron.

The outer surface shell of dendritic polymers, including dendrimers and dendrons, may contain either chemically reactive or passive functional capping groups. Chemically reactive capping groups can be used for further extension of dendritic growth or for modification of dendritic molecular surfaces. The chemically passive capping groups may be used to physically modify dendritic surfaces, such as to adjust the ratio of hydrophobic, or lipophilic, to hydrophilic, or lipophobic, terminals, and/or to improve the solubility of the dendritic polymer, dendrimer, or dendron, for a particular solvent.

As used herein, the term "lipophilic dendron" refers to a dendron having one or more capping groups comprising an alkyl group having at least 6 carbon atoms, typically at least 10 carbon atoms, more typically at least 12 carbon atoms.

In an embodiment, the at least one dendron attached to the surface of the metallic core comprises the structure of formula (I) or (II):

$$\text{—S—L}_1\text{—}\overset{\overset{O}{\|}}{\underset{R_1}{C}}\text{—}\begin{bmatrix}D_1\text{—O—}R_2\\D_2\text{—O—}R_3\end{bmatrix}_n \quad (I)$$

$$\text{—S—L}_1\text{—R}_2 \quad (II)$$

wherein
each occurrence of $R_1$ is H or $C_1$-$C_{20}$ alkyl,
each occurrence of $D_1$ and $D_2$ are each, independently, $C_1$-$C_{20}$ alkylene,
each occurrence of $L_1$ is $C_1$-$C_{20}$ alkylene,
each occurrence $R_2$ and $R_3$ are each, independently, H, $C_1$-$C_{38}$ alkyl, $C_2$-$C_{38}$ alkenyl, or $C_2$-$C_{38}$ alkynyl,
n is from 1 to 6;
wherein $R_1$, $D_1$, and $D_2$, $L_1$, $R_2$, and $R_3$, are each optionally interrupted by one or more divalent moieties;
and is attached to the metallic core via the sulfur atom.

$R_1$, $D_1$, $D_2$, $L_1$, $R_2$, and $R_3$, as defined herein, may optionally be interrupted by one or more divalent moieties.

As used herein, the phrase "interrupted by one or more divalent moieties" when used in relation to a substituent means a modification to the substituent in which one or more divalent moieties are inserted into one or more covalent bonds between atoms.

The interruption may be in a carbon-carbon bond, a carbon-hydrogen bond, a carbon-heteroatom bond, a hydrogen-heteroatom bond, or heteroatom-heteroatom bond. The interruption may be at any position in the substituent modified, even at the point of attachment to another structure.

The one or more divalent moieties may be selected from the group consisting of the following:

$$*\text{—}\underset{R_b}{\overset{R_a}{\underset{|}{\overset{|}{C}}}}\text{—}*, \quad *\text{—}\underset{R_c}{\overset{|}{C}}\text{=}\underset{R_d}{\overset{|}{C}}\text{—}*, \quad *\text{—}\underset{R_e}{\overset{|}{N}}\text{—}\underset{R_f}{\overset{|}{N}}\text{—}*,$$

$$*\text{—}\underset{R_g}{\overset{|}{N}}\text{—}*, \quad *\text{—}\overset{O}{\overset{\|}{C}}\text{—}\underset{R_h}{\overset{|}{N}}\text{—}*, \quad *\text{—}\underset{R_i}{\overset{|}{N}}\text{—}\overset{S}{\overset{\|}{C}}\text{—}S\text{—}*,$$

$$*\text{—O—}*, \quad *\text{—S—}*, \quad *\text{—S—S—}*, \quad *\text{—}\overset{O}{\overset{\|}{C}}\text{—}*,$$

$$*\text{—}\overset{S}{\overset{\|}{C}}\text{—}*, \quad *\text{—}\overset{O}{\overset{\|}{S}}\text{—}*, \quad *\text{—}\overset{\overset{O}{\|}}{\underset{\underset{O}{\|}}{S}}\text{—}*, \quad *\text{—}\overset{\overset{O}{\|}}{\underset{\underset{O}{\|}}{S}}\text{—O—}*,$$

$$*\text{—O—}\overset{\overset{O}{\|}}{\underset{\underset{O}{\|}}{S}}\text{—O—}*, \quad *\text{—}\overset{O}{\overset{\|}{C}}\text{—O—}*, \quad *\text{—C≡C—}*,$$

$$*\text{—}\underset{*}{\underset{\bigcirc}{\phantom{.}}}\text{—}*, \quad \underset{*}{\overset{*\text{—}}{\underset{N}{\underset{|}{\overset{N\text{≈}N}{\phantom{.}}}}}}, \quad *\text{—}\underset{R_k}{\overset{R_j}{\underset{|}{\overset{|}{Si}}}}\text{—O—}*$$

and $*\text{—N≡N—}*$.

As used herein, the asterisks indicate a point of connection.

Each occurrence of $R_a$-$R_k$, are each, independently H, halogen, typically F, or alkyl. When any of $R_a$-$R_k$ is alkyl, the alkyl group may optionally be interrupted by one or more divalent moieties defined herein.

The generation n is, typically, 1 to 6, still more typically, 1 to 4.

In an embodiment, $R_1$ is methyl.

In an embodiment, $D_1$ and $D_2$ are each methylene.

In an embodiment, $R_2$ and $R_3$ are each $C_{17}$-alkyl. In another embodiment, $R_2$ and $R_3$ are each $C_{17}$-alkyl interrupted by $$*\text{—}\overset{O}{\overset{\|}{C}}\text{—}*.$$

In an embodiment, $L_1$ is $C_{12}$-alkylene. In another embodiment, $L_1$ is $C_{12}$-alkylene interrupted by —O— and $$\underset{*}{\overset{*\text{—}}{\underset{N}{\underset{|}{\overset{N\text{≈}N}{\phantom{.}}}}}}.$$

The present disclosure relates to a film comprising a plurality of hybrid nanoparticles described herein. The plurality of hybrid nanoparticles may comprise hybrid nanoparticles that have the same or different effective diameter.

In an embodiment, the plurality of hybrid nanoparticles comprises hybrid nanoparticles having the same effective diameter.

In an embodiment, the plurality of hybrid nanoparticles forms a hexagonal close-packed (hcp) assembly.

In another embodiment, the plurality of hybrid nanoparticles comprises hybrid nanoparticles that have different effective diameters.

In an embodiment, the plurality of hybrid nanoparticles forms a solid phase isostructural with $NaZn_{13}$.

In another embodiment, the plurality of hybrid nanoparticles forms a solid phase isostructural with $CaCu_5$.

Various properties of the hybrid nanoparticles of the present disclosure, and of films containing the hybrid nanoparticles, may be determined using methods and instruments known to those of ordinary skill in the art.

The absorption wavelength of the hybrid nanoparticles and/or film comprising a plurality of the hybrid nanoparticles may be measured according to methods and instruments known to those of ordinary skill in the art. For example, optical extinction spectra may be obtained using a Cary 5000 UV-VIS-NIR for solid films and solution-phase measurements may be obtained on an Analytical Spectral Devices QSP 350-2000 UV-VIS-NIR spectrometer. Typically, the maximum absorption wavelength ($\lambda_{max}$) of the hybrid nanoparticles is from about 520 nm to about 560 nm, more typically from about 525 nm to about 540, still more typically from about 528 to 535.

The effective diameter of the hybrid nanoparticles, designated $\Phi_{hyb}$, may be determined using one or more techniques and instruments known to those of ordinary skill in the art. For example, a combination of techniques including NMR and UV-Vis spectroscopies, thermogravimetric analysis (TGA), transmission electron microscopy (TEM) and small-angle X-ray scattering (SAXS) may be used. TGA may be carried out using a TA Instruments TGA Q600 apparatus in the temperature range of 25° C. to 500° C. under $N_2$ flow at a heating rate of 30° C./min, with thermal transitions being determined on a TA Instruments Q2000 differential scanning calorimeter (DSC) equipped with a liquid nitrogen cooling system with 10° C./min heating and cooling rates. SAXS may be performed using a Multi-angle X-ray scattering instrument equipped with a Bruker Nonius FR591 40 kV rotating anode generator operated at 85 mA, Osmic Max-Flux optics, 2D Hi-Star Wire detector, and pinhole collimation, with an evacuated beam path.

The effective diameter of the hybrid nanoparticles, designated $\Phi_{hyb}$, is given by the equation $$\Phi_{hyb}=2[(\Phi/2)^3/(1-f)]^{1/3},$$

wherein $\Phi$ is the metallic core diameter and f is the ligand, or dendron, volume fraction, which is given by the equation $$f=n_L V_L/(n_L V_L+V_{M@NP}),$$

wherein $n_L$ is the number of ligands, or dendrons, grafted on the surface of the metallic core, $V_L$ is the volume of the ligands, or dendrons, estimated assuming a density of 0.9 g cm$^{-3}$, and $V_{M@NP}$ is the volume of the metal in the hybrid nanoparticle.

The metallic core diameter of the hybrid nanoparticles described herein is typically from about 1 nm to about 100 nm, more typically from about 1 to about 60 nm. In an embodiment, the metallic core diameter is from about 1 to about 6 nm. In another embodiment, the metallic core diameter is from about 20 to about 60 nm.

For hybrid nanoparticles having metallic core diameter of less than 15 nm, the number of ligands, or dendrons, grafted on the surface of the metallic core, designated $n_L$, is given by the equation $$n_L = \left(\frac{wt \%(L)}{1-wt \%(L)}\right)\left(\frac{MW_{M@NP}}{MW_L}\right),$$

wherein wt % (L) is the weight fraction of the ligands, or dendrons, $MW_{M@NP}$ is the weight of metal per mole of the hybrid nanoparticle, and $MW_L$ is the molecular weight of the ligands, or dendrons.

The weight of the metal per mole of the hybrid nanoparticle, $MW_{M@NP}$, is determined by multiplying the number of metal atoms in the particle with the molecular weight of the metal, and the number of metal atoms can be determined using methods known to the ordinarily-skilled artisan. For example, the diameter of the metallic core, $\Phi$, can be used to calculate the volume of the metallic core, assuming a spherical core, and dividing the result by the volume of one atom of the metal.

The weight fraction of the ligands, or dendrons, wt % (L), can be determined by TGA measurements.

The effective diameter of the hybrid nanoparticles described herein are, typically from about 9 nm to about 15 nm, more typically from about 10 to about 13 nm.

In another embodiment, the effective diameter of the hybrid nanoparticles described herein is at least 20 nm, at least 30 nm, at least 40 nm, or at least 50 nm.

Interparticle distance, designated a, of the hybrid nanoparticles, for example, in a film, may be determined by TEM microscopy or by SAXS. Interparticle spacing, designated a, is given by the equation $$a=[3d \log 3]/\pi,$$

wherein d is the diffraction spacing, which is equal to $2\pi/q$, where q is the q-vector (from SAXS).

Interparticle distance, designated a, is typically from about 9 nm to about 15 nm, more typically from about 9.5 to about 12 nm.

Edge-to-edge separation, designated s, of the hybrid nanoparticles, for example, in a film, is given by the equation $$s=a-\Phi,$$

wherein a and $\Phi$ are defined herein.

Edge-to-edge separation is typically from about 3 nm to about 10 nm, more typically from about 3.5 nm to 7.5 nm, still more typically from about 3.5 nm to about 6.5 nm.

Further information on the equations described herein may be found in Marcos, M.; Giménez, R.; Serrano, J. L.; Donnio, B.; Heinrich, B.; Guillon, D. *Chem. Eur. J.* 2001, 7, 1006.

The present disclosure also relates to a dendrimer represented by the structure of formula (III) or (IV):

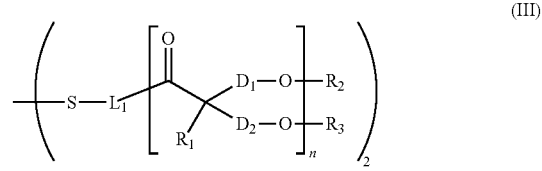

wherein
each occurrence of $R_1$ is H or $C_1$-$C_{20}$ alkyl,
each occurrence of $D_1$ and $D_2$ are each, independently, $C_1$-$C_{20}$ alkylene,
each occurrence of $L_1$ is $C_1$-$C_{20}$ alkylene,
each occurrence $R_2$ and $R_3$ are each, independently, H, $C_1$-$C_{38}$ alkyl, $C_2$-$C_{38}$ alkenyl, or $C_2$-$C_{38}$ alkynyl,
n is from 1 to 6;

wherein $R_1$, $D_1$, and $D_2$, $L_1$, $R_2$, and $R_3$, are each optionally interrupted by one or more divalent moieties defined herein.

The generation n is, typically, 1 to 6, still more typically, 1 to 4.

In an embodiment, $R_1$ is methyl. In an embodiment, $D_1$ and $D_2$ are each methylene.

In an embodiment, $R_2$ and $R_3$ are each $C_{17}$-alkyl. In another embodiment, $R_2$ and $R_3$ are each $C_{17}$-alkyl interrupted by

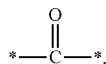

In an embodiment, $L_1$ is $C_{12}$-alkylene. In another embodiment, $L_1$ is $C_{12}$-alkylene interrupted by —O— and

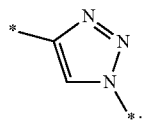

The present disclosure relates to a method for producing the dendrimer described herein, the method comprising:
reacting a compound represented by the structure of formula (V):

$$G_1\text{-S—S-}G_1 \tag{V}$$

with a compound represented by the structure of formula (VI) or (VII):

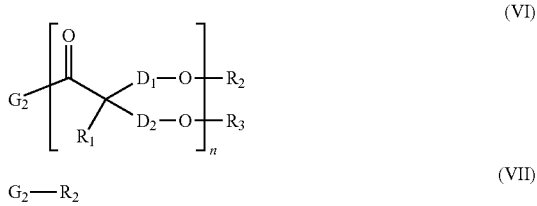

wherein
each occurrence of $R_1$ is H or $C_1$-$C_{20}$ alkyl,
each occurrence of $D_1$ and $D_2$ are each, independently, $C_1$-$C_{20}$ alkylene,
each occurrence $R_2$ and $R_3$ are each, independently, H, $C_1$-$C_{38}$ alkyl, $C_2$-$C_{38}$ alkenyl, or $C_2$-$C_{38}$ alkynyl,
n is from 1 to 6;
  wherein $R_1$, $D_1$, and $D_2$, $R_2$, and $R_3$, are each optionally interrupted by one or more divalent moieties defined herein;
each occurrence of $G_1$ is a substituent comprising a reactive group capable of reacting with the reactive group in $G_2$, and
$G_2$ is a substituent comprising a reactive group capable of reacting with the reactive group in $G_1$.

The generation n is, typically, 1 to 6, still more typically, 1 to 4.

In an embodiment, $R_1$ is methyl.
In an embodiment, $D_1$ and $D_2$ are each methylene.
In an embodiment, $R_2$ and $R_3$ are each $C_{17}$-alkyl. In another embodiment, $R_2$ and $R_3$ are each $C_{17}$-alkyl interrupted by

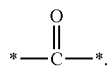

$G_1$ is a substituent comprising a reactive group capable of reacting with the reactive group in $G_2$, and $G_2$ is a substituent comprising a reactive group capable of reacting with the reactive group in $G_1$.

Typically, $G_1$ is a $C_1$-$C_{15}$-alkyl group, optionally interrupted by one or more divalent moieties defined herein, comprising a reactive group capable of reacting with the reactive group in $G_2$.

In an embodiment, G1 comprises a reactive group selected from the group consisting of —X, —NH$_2$, —N$_3$, —(C=O)X, —Ph(C=O)X, —SH, —CH=CH$_2$, —C≡CH; wherein X is a leaving group.

In an embodiment, $G_1$ is a $C_1$-$C_{15}$-alkyl group comprising a —N$_3$ group.

Typically, $G_2$ is a $C_1$-$C_{15}$-alkyl group, optionally interrupted by one or more divalent moieties defined herein, comprising a reactive group capable of reacting with the reactive group in $G_1$.

In an embodiment, $G_2$ comprises a reactive group selected from the group consisting of —(C=O)X, —CH=CH$_2$, —C≡CH, —NH$_2$, —N$_3$, —Ph(C=O)X, —SH, —X, —NCO, —NCS; wherein X is a leaving group.

Leaving groups are known to those of ordinary-skill in the art. Suitable leaving groups include, but are not limited to, halides, such as, fluoride, chloride, bromide, and iodide; alkyl and aryl sulfonates, such as methanesulfonate (mesylate) and p-toluenesulfonate (tosylate); and hydroxide.

In an embodiment, $G_2$ is a $C_1$-$C_{15}$-alkyl group comprising a —C≡CH group, and is interrupted by a —O— group.

According to the present disclosure, it is understood that the reactive groups on $G_1$ and $G_2$ may be reversed.

The compounds represented by the structures of formulae (V), (VI), and (VII) may be obtained from commercial sources or synthesized according to synthetic methods well-known to those of ordinary skill in the art. Suitable synthetic methods known to those of ordinary skill in the art are described in well-known texts, including, but not limited to, M. B. Smith "March's Advanced Organic Chemistry: Reactions, Mechanisms, and Structure", 7$^{th}$ edition (Wiley); and Carey and Sunberg "Advanced Organic Chemistry, Part A: Structure and Mechanisms", 5$^{th}$ edition (Springer) and "Advanced Organic Chemistry: Part B: Reaction and Synthesis", 5$^{th}$ edition (Springer).

Any suitable reaction conditions, including reaction vessels and equipment, for the reacting step may be selected by the ordinary-skilled artisan according to concepts known in the chemical arts.

The present disclosure relates to a method for producing the hybrid nanoparticle described herein, the method comprising:
(i) producing the dendrimer described herein, and
(ii) contacting the dendrimer produced in step (i) with a metallic nanoparticle;
thereby producing the hybrid nanoparticle.

Production of the dendrimer described herein may be achieved using any method known to the ordinarily-skilled artisan. Typically, the dendrimer is produced using the method for producing the dendrimer described herein.

Subsequent to producing the dendrimer described herein, the dendrimer is contacted with a metallic nanoparticle. The metallic nanoparticle becomes the metallic core of the hybrid nanoparticle.

The metallic nanoparticle may be obtained from commercial sources or made according to methods known in the art. The metallic nanoparticle comprises or consists of a metal, or an alloy or intermetallic comprising a metal. Metals include, for example, main group metals such as, e.g., lead, tin, bismuth, antimony and indium, and transition metals, e.g., a transition metal selected from the group consisting of gold, silver, copper, nickel, cobalt, palladium, platinum, iridium, osmium, rhodium, ruthenium, rhenium, vanadium, chromium, manganese, niobium, molybdenum, tungsten, tantalum, titanium, zirconium, zinc, mercury, yttrium, iron and cadmium. The metallic nanoparticle may comprise or consist of oxides of the metals described herein.

In an embodiment, the metallic nanoparticle comprises a transition metal.

In an embodiment, the metallic nanoparticle comprises gold.

The metallic nanoparticle, prior to contact with the dendrimer, may optionally comprise organic capping groups, such as, for example, oleylamine or CTAB.

The contacting step may be carried out according to any method. For example, the metallic nanoparticle may be suspended in one or more solvents described herein to form a first mixture. The dendrimer described herein may be dissolved in one or more solvents described herein to form a second mixture. The first and second mixtures may then be combined and stirred, thereby producing the hybrid nanoparticle.

The present disclosure relates to a composition comprising at least one hybrid nanoparticle described herein and a liquid carrier.

The composition of the present disclosure may be a dispersion in which the at least one hybrid nanoparticle is not solubilized, but suspended in the liquid carrier.

The liquid carrier used in the composition according to the present disclosure comprises an organic solvent or a blend of organic solvents. In an embodiment, the composition consists essentially of or consists of an organic solvent or a blend of organic solvents. The blend of organic solvents comprises two or more organic solvents.

Organic solvents suitable for use in the liquid carrier may be polar or non-polar, protic or aprotic solvents. Examples of suitable organic solvents include, but are not limited to, chlorinated solvents, such as, for example, chloroform and dichloromethane; alkane solvents, such as, for example, pentane, hexane, heptane, and isomers thereof; and alcohols, such as, for example, n-propanol, isopropanol, ethanol, and methanol, and alkylene glycol monoethers.

In an embodiment, the liquid carrier comprises hexane, or isomers thereof.

The liquid carrier of the composition according to the present disclosure may further comprise a residual amount of water as a result of, for example, hygroscopic uptake by the solvents of the liquid carrier or carry-over from the reaction medium used to make the metallic nanoparticles. The amount of water in the composition is from 0 to 2% wt., with respect to the total amount of composition. Typically, the total amount of water in the composition is from 0 to 1% wt, more typically from 0 to 0.5% wt, still more typically from 0 to 0.1% wt, with respect to the total amount of the composition. In an embodiment, the composition of the present disclosure is free of water.

The amount of liquid carrier in the composition according to the present disclosure is from about 50 wt. % to about 99 wt. %, typically from about 75 wt. % to about 99 wt. %, still more typically from about 90 wt. % to about 99 wt. %, with respect to the total amount of composition.

The present disclosure relates to method for producing the film described herein, the method comprising:
(i) coating a composition described herein on the surface of a liquid immiscible with the liquid carrier of the composition, and
(ii) removing the liquid carrier of the composition, thereby producing the film.

The step of coating a composition described herein on the surface of a liquid immiscible with the liquid carrier of the composition may be achieved using any method known to the ordinarily-skilled artisan. For example, a drop of the composition may be spread on the surface of a liquid immiscible with the liquid carrier of the composition.

The liquid immiscible with the liquid carrier of the composition may be any solvent or blend of solvents that is immiscible with the liquid carrier of the composition. In an embodiment, the liquid immiscible with the liquid carrier of the composition is diethylene glycol.

Subsequent to the coating step, the step of removing the liquid carrier of the composition may be achieved according to any method known to the ordinarily-skilled artisan. For example, the liquid carrier of the composition may be allowed to evaporate under temperatures and pressures selected by the artisan based on the liquid carrier to be removed. In an embodiment, the step of removing the liquid carrier of the composition is carried out under ambient temperature and pressure.

The present disclosure also relates to a method for producing a ring structure comprising a plurality of the hybrid nanoparticles described herein, the method comprising:
(i) coating a composition described herein, the liquid carrier of which comprises a residual amount of water, on the surface of a support, and
(ii) removing the liquid carrier of the composition, thereby producing the ring structure.

The step of coating a composition described herein, in which the liquid carrier comprises a residual amount of water, on the surface of a support, may be achieved by using any method known to the ordinarily-skilled artisan. For example, a drop of the composition may be spread on the surface of the support. Suitable support materials include, for example, glass; ceramic; metal, for example, copper, nickel, gold, stainless steel, titanium, molybdenum, aluminum, rhodium, and the like; and plastic films.

Subsequent to the coating step, the step of removing the liquid carrier of the composition may be achieved according to any method known to the ordinarily-skilled artisan. For example, the liquid carrier of the composition may be allowed to evaporate under temperatures and pressures selected by the artisan based on the liquid carrier to be removed.

The hybrid nanoparticles, compositions, methods and processes, and films according to the present disclosure are further illustrated by the following non-limiting examples.

EXAMPLES

The materials used in the following examples, unless otherwise stated, are summarized below.

2,2-Dimethoxypropane (98+%), bis-MPA (98%), propargyl bromide (80% soln. in toluene), propargyl alcohol (99%), pyridine (reagent), Dowex $H^+$ ion exchange resin (200-400 mesh), p-toluenesulfonyl chloride (TsCl, 99+%), thiourea (99%), dodecanethiol (DDT, 99%), 1,2,3,4-tetrahydronapthalene (tetralin, ≥98%), borane tert-butylamine complex (TBAB, 95%), $HAuCl_4.3H_2O$ (ACS Reagent), copper (II) sulfate pentahydrate (98+), triethylamine ($Et_3N$, 99%) and oleylamine (80-90%) were purchased from Acros Organics and used without further purification. N,N'-Dicyclohexylcarbodiimide (DCC, 99%), $NaN_3$ (≥99.5%), 4-dimethylaminopyridine (DMAP, 99%), stearic anhydride (≥97%), sodium L-ascorbate (≥99%) and 11-bromo-1-undecanol (98%) were purchased from Sigma-Aldrich and used without further purification. Solvents were ACS grade or higher. $CH_2Cl_2$ was dried over $CaH_2$ and freshly distilled before used. $HAuCl_4.3H_2O$ was stored in a 4° C. refrigerator.

In general, unless otherwise stated, $^1H$ NMR (500 MHz) and $^{13}C$ NMR (126 MHz) spectra were recorded on Bruker UNI500 or BIODRX500 NMR spectrometer. $^1H$ and $^{13}C$ chemical shifts (δ) are reported in ppm while coupling constants (J) are reported in Hertz (Hz). The multiplicity of signals in $^1$H NMR spectra is described as "s" (singlet), "d" (doublet), "t" (triplet), "q" (quartet), "p" (pentet), "dd" (doublet of doublets) and "m" (multiplet). All spectra were referenced using solvent residual signals (CDCl$_3$: $^1$H, δ 7.27 ppm; $^{13}$C, δ 77.2 ppm, MeOD: $^1$H, δ 3.31 ppm; $^{13}$C, δ 49.00 ppm). 2D one bond heteronuclear correlation $^1$H-$^{13}$C HSQC experiment was used to confirm NMR peak assignments.

Reaction progress was monitored by thin-layer chromatography using silica gel coated plates or $^1$H NMR. Compounds were purified by filtration, precipitation, crystallization and/or flash column chromatography using silica gel (Acros Organics, 90 Å, 35-70 μm) as indicated.

Matrix-assisted laser desorption/ionization time of flight (MALDI-TOF) mass spectrometry was performed on Bruker Ultraflex III (Maldi-Tof-Tof) mass spectrometer using dithranol as matrix.

Example 1. Synthesis of G1 Dendrimer (Compound 17)

Initially, 1,2-bis(11-azidoundecyl)disulfane (compound 4) was synthesized according to Scheme 1 below.

(17.9 g, 93.8 mmol) in dry CH$_2$Cl$_2$ (300 mL) was added triethylamine (14.23 g, 140.6 mmol) drop wise (over a period of 30 min.) and the resulting mixture was allowed to warm up to 23° C. The stirring was continued under nitrogen atmosphere for additional 12 h. The mixture was diluted with additional CH$_2$Cl$_2$ (200 mL) and washed with 1N HCl (3×100 mL), dried over anhydrous MgSO$_4$ and concentrated under reduced pressure. The residue was purified by column chromatography (SiO$_2$, 0-50% EtOAc:hexanes) to afford pure 11-azidoundecyl 4-methylbenzenesulfonate 3 (29.63 g, 86%) as a colorless oil. $^1$H NMR (CDCl$_3$) δ 7.75 (d, J=8.4 Hz, 2H), 7.31 (d, J=8.0 Hz, 2H), 3.98 (t, J=6.5 Hz, 2H), 3.22 (t, J=6.9 Hz, 2H), 2.41 (s, 3H), 1.65-1.50 (m, 4H), 1.35-1.15 (m, 14H); $^{13}$C NMR (CDCl$_3$) δ 144.63, 133.18, 129.78, 127.81, 70.68, 51.42, 29.36, 29.31, 29.28, 29.07, 28.85, 28.79, 28.76, 26.66, 25.28, 21.57.

1,2-Bis(11-azidoundecyl)disulfane (4)

To a stirred solution of 11-azidoundecyl 4-methylbenzenesulfonate 3 (20 g, 54.4 mmol) in ethanol (50 mL) was added thiourea (4.57 g, 60 mmol) and the resulting mixture stirred at 80° C. for 12 h. The reaction mixture was cooled to 23° C., basified using 2N NaOH (60 mL) and stirred for 20 min. The mixture was then acidified with 2N H$_2$SO$_4$ (70

Scheme 1.

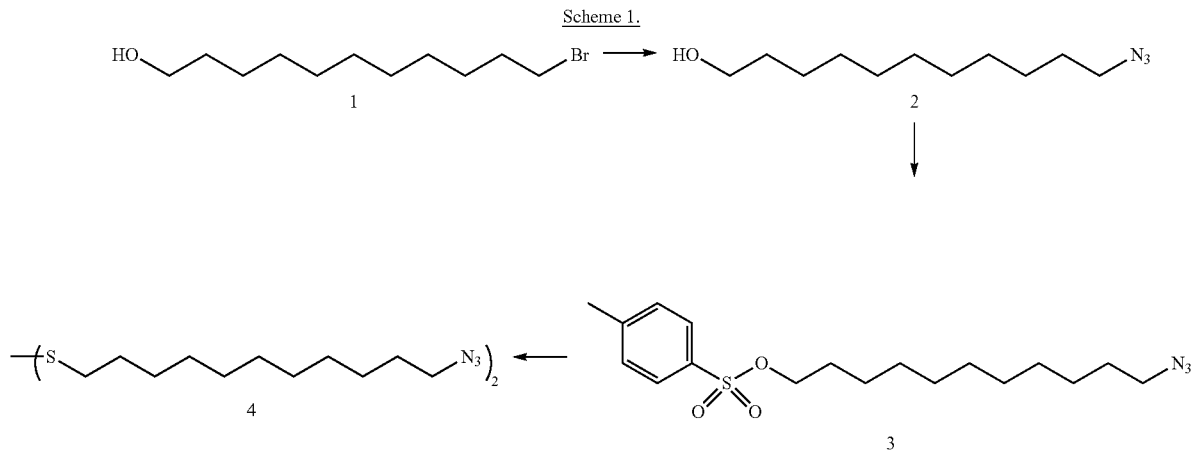

11-Azidoundecan-1-ol (2)

To a solution of 1-bromoundecanol 1 (30 g, 119.4 mmol) in DMF (150 mL) was added NaN$_3$ (15.5 g, 238.9 mmol) and the resulting mixture was stirred at 70° C. for 12 h. The mixture was cooled to 23° C., filtered and the filtrate extracted with hexane (5×200 mL). The hexanes fractions were combined and washed with H$_2$O (2×100 mL), dried over anhydrous Na$_2$SO$_4$ and concentrated under reduced pressure to afford 11-azidoundecan-1-ol 2 (24.19 g, 95%) as a colorless oil. $^1$H NMR (CDCl$_3$) δ 3.62 (t, J=6.6 Hz, 2H), 3.24 (t, J=6.9 Hz, 2H), 1.61-1.51 (m, 4H), 1.39-1.24 (m, 14H); $^{13}$C NMR (CDCl$_3$) δ 63.15, 51.60, 32.89, 29.66, 29.56, 29.51, 29.25, 28.95, 26.82, 25.84.

11-Azidoundecyl 4-methylbenzenesulfonate (3)

To a stirred, cooled (0° C.) mixture of 11-azido-1-undecanol 2 (20 g, 93.8 mmol) and p-toluenesulfonyl chloride mL), concentrated under reduced pressure and extracted with CH$_2$Cl$_2$ (3×100 mL). Organic layer was dried over anhydrous Na$_2$SO$_4$, filtered and the filtrate concentrated. The residue was mixed with MeOH (50 mL) and treated with solution of iodine (1M solution in MeOH) until color of suspension turned yellow. Na$_2$SO$_3$ was then added to remove the excess iodine and the mixture concentrated under reduced pressure. The residue was extracted with CH$_2$Cl$_2$ (2×100 mL), concentrated under reduced pressure and purified by column chromatography (SiO$_2$, 0-50% CHCl$_3$:hexanes) to afford 1,2-bis(11-azidoundecyl)disulfane 4 (8.7 g, 70%) as a colorless liquid. $^1$H NMR (CDCl$_3$) δ 3.25 (t, J=6.9 Hz, 4H), 2.67 (t, J=7.4 Hz, 4H), 1.66 (p, J=7.4 Hz, 4H), 1.59 (p, J=7.1 Hz, 4H), 1.42-1.33 (m, 8H), 1.33-1.25 (m, 20H); $^{13}$C NMR (CDCl$_3$) δ 51.60, 39.29, 29.57, 29.33, 29.26, 28.96, 28.62, 26.83.

2-Methyl-2-((prop-2-yn-1-yloxy)carbonyl)propane-1,3-diyldistearate (compound 12) was then synthesized according to Scheme 2 below.

Scheme 2

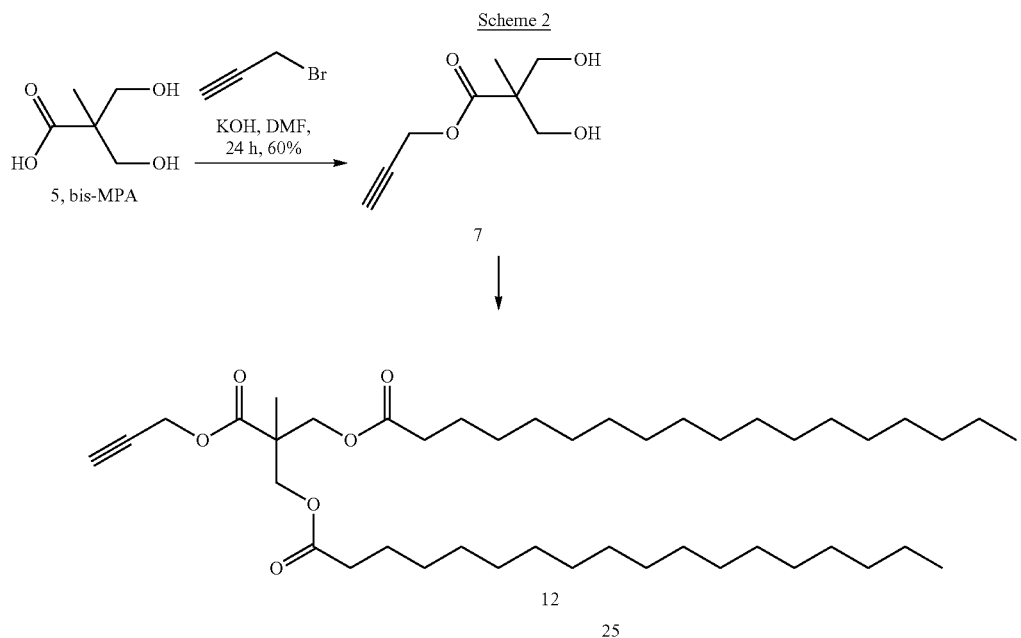

To a stirred solution of 2,2-bis(hydroxyl methyl)-propionic acid (compound 5) (18 g, 136.3 mmol) in DMF (100 mL) was added KOH (8.2 g, 146.6 mmol). The resulting solution was stirred at 100° C. for 2 h after which propargyl bromide (20.3 g, 137 mmol) was added dropwise (over 30 min) and stirring continued for an additional 48 h. The solution was cooled to 23° C., filtered and DMF was evaporated under reduced pressure. The residue was dissolved in chloroform (70 mL), filtered and the filtrate placed in the fridge at −10° C. for 2 h. The resulting white precipitate was quickly filtered and dried to afford prop-2-yn-1-yl 3-hydroxy-2-(hydroxymethyl)-2-methylpropanoate (compound 7) (13.8 g, 60%) as a white solid. $^1$H NMR (CDCl$_3$) δ 4.73 (d, J=2.5 Hz, 2H), 3.88 (d, J=11.4 Hz, 2H), 3.70 (d, J=13.1 Hz, 2H), 3.30-2.74 (m, 2H), 2.49 (t, J=2.4 Hz, 1H), 1.09 (s, 3H); $^{13}$C NMR (CDCl$_3$) δ 175.13, 77.47, 75.37, 67.33, 52.56, 49.49, 17.12.

To a stirred solution of compound 7, DMAP and pyridine in CH$_2$Cl$_2$ (50 mL) was added stearic anhydride and the resulting mixture stirred for 12 h. The reaction mixture was diluted with additional CH$_2$Cl$_2$ (50 mL), washed with 1N HCl (3×50 mL), dried over anhydrous MgSO$_4$, filtered and filtrate concentrated under reduced pressure. The residue was purified by column chromatography (SiO$_2$, 0-50% EtOAc:hexanes) to afford compound 12 (2.3 g, 92%). Compound 12 was further purified by repeated precipitation from CHCl$_3$/MeOH. $^1$H NMR (CHCl$_3$) δ 4.68 (d, J=2.5 Hz, 2H), 4.23 (d, J=11.0 Hz, 2H), 4.20 (d, J=11.1 Hz, 2H), 2.44 (t, J=2.5 Hz, 1H), 2.27 (t, J=7.6 Hz, 4H), 1.57 (t, J=7.3 Hz, 4H), 1.30-1.20 (m, 59H), 0.85 (t, J=6.9 Hz, 6H); $^{13}$C NMR (CDCl$_3$) δ 173.26, 172.14, 77.27, 75.19, 65.19, 52.62, 46.46, 34.19, 32.04, 29.81, 29.79, 29.77, 29.72, 29.58, 29.48, 29.37, 29.23, 24.97, 22.80, 17.77, 14.21.

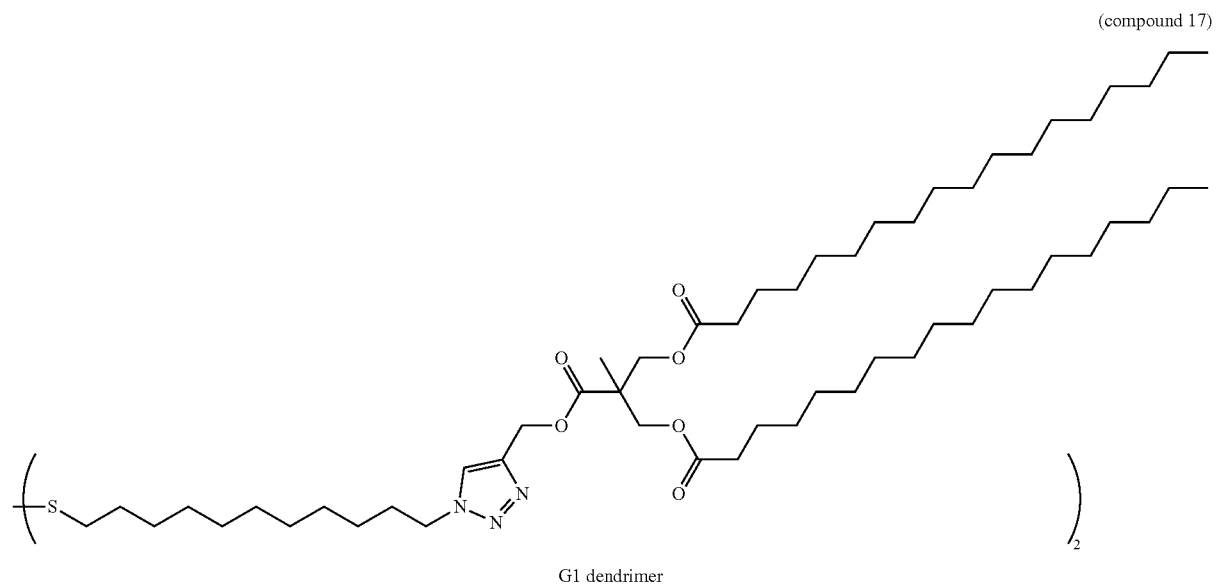

(compound 17)

G1 dendrimer

The G1 dendrimer (compound 17) was formed by coupling compound 4 and compound 12. To a stirred solution of prop-2-yn-1-yl stearate, compound 12 (6.2 mmol), compound 4 (1.42 g, 3.1 mmol) and $CuSO_4 \cdot 5H_2O$ (0.3 g, 1.24 mmol) in $THF/H_2O$ 4:1 (10 mL) was added sodium ascorbate (0.49 g, 2.48 mmol) and the resulting mixture stirred at 60° C. for 2 h under microwave irradiation (constant temperature mode). The solvent was evaporated, residue was dissolved in $CHCl_3$ (100 mL) and washed with 1N HCl (3×20 mL). The organic layer was dried over anhydrous $Na_2SO_4$, filtered and the filtrate concentrated under reduced pressure. The crude product was purified by column chromatography ($SiO_2$, 0-100% EtOAc:hexanes) to afford compound 17 as a white solid (0.9 g, 90%). $^1H$ NMR ($CDCl_3$) δ 7.57 (s, 2H), 5.25 (s, 4H), 4.33 (t, J=7.4 Hz, 4H), 4.22 (d, J=11.0 Hz, 4H), 4.18 (d, J=11.1 Hz, 4H), 2.66 (t, J=7.4 Hz, 4H), 2.24 (t, J=7.6 Hz, 8H), 1.90 (t, J=7.1 Hz, 4H), 1.66 (p, J=7.4 Hz, 4H), 1.55 (p, J=6.9 Hz, 4H), 1.41-1.22 (m, 140H), 1.21 (s, 6H), 0.87 (t, J=6.7 Hz, 12H); $^{13}C$ NMR ($CDCl_3$) δ 173.38, 172.93, 145.70, 123.70, 65.22, 58.56, 50.59, 46.48, 39.23, 34.21, 32.07, 30.42, 29.85, 29.81, 29.77, 29.64, 29.60, 29.52, 29.51, 29.41, 29.37, 29.34, 29.27, 29.13, 28.65, 26.64, 24.99, 22.83, 17.87, 14.27; MALDI-TOF (m/z): $[M+Na]^+$ calcd. for $C_{110}H_{204}N_6O_{12}S_2$, 1888.4876; found 1888.681.

Example 2. Synthesis of G2 Dendrimer

Compound 13 was initially synthesized according to Scheme 3 below.

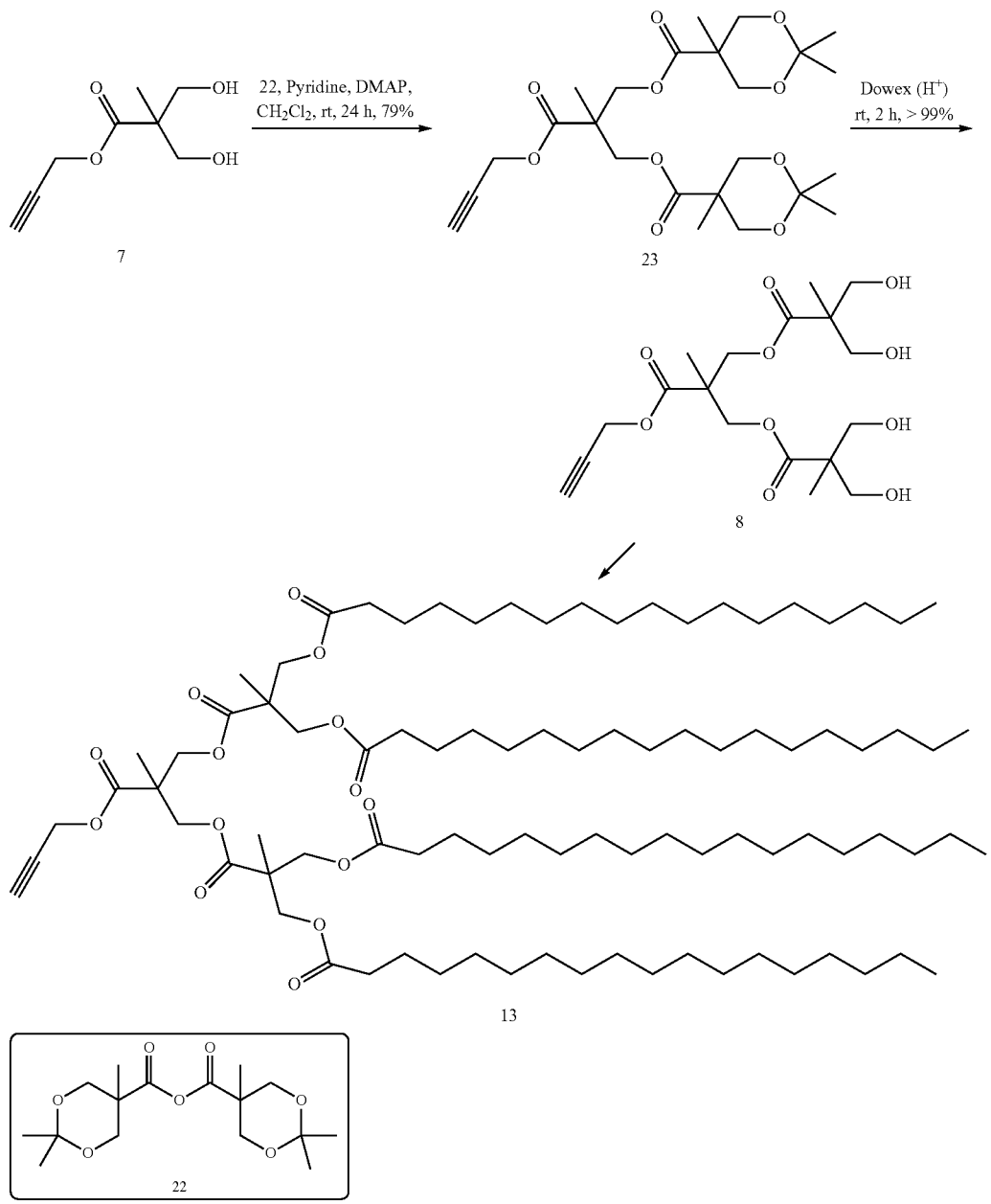

To a stirred solution of prop-2-yn-1-yl 3-hydroxy-2-(hydroxymethyl)-2-methylpropanoate, 7 (8.0 g, 46.5 mmol), DMAP (2.27 g, 18.6 mmol) and pyridine (11.0 g, 139.4 mmol) in $CH_2Cl_2$ (100 mL) was added 2,2,5-trimethyl-1,3-dioxane-5-carboxylic anhydride, 22 (36.8 g, 111.5 mmol) and the resulting mixture stirred for 24 h. Compound 22 was synthesized according to published procedures (see Ihre, H.; Hult, A.; Fréchet, J. M. J.; Gitsov, I. *Macromolecules* 1998, 31, 4061; and Gillies, E. R.; Fréchet, J. M. J. *J. Am. Chem. Soc.* 2002, 124, 14137). The reaction was quenched with 5 mL water and diluted with additional $CH_2Cl_2$ (200 mL), washed with $NaHSO_4$ (2×100 mL), $Na_2CO_3$ (2×100 mL) and brine (50 mL), dried over anhydrous $MgSO_4$ and concentrated under reduced pressure. The residue was purified by column chromatography ($SiO_2$, 0-50% EtOAc:hexanes) to afford the title compound, 23 (17.8 g, 79%). $^1$H NMR ($CDCl_3$) δ 4.72 (d, J=2.6 Hz, 2H), 4.37-4.28 (m, 4H), 4.15 (d, J=12.0 Hz, 4H), 3.62 (d, J=10.9 Hz, 4H), 2.46 (t, J=2.4 Hz, 1H), 1.41 (s, 6H), 1.36 (s, 6H), 1.31 (s, 3H), 1.15 (s, 6H); $^{13}$C NMR ($CDCl_3$) δ 173.58, 171.92, 98.18, 77.30, 75.43, 66.06, 66.03, 65.35, 52.76, 46.90, 42.15, 25.11, 22.31, 18.60, 17.68; MALDI-TOF (m/z): [M+Na]$^+$ calcd. for $C_{24}H_{36}O_{10}Na$, 507.2206; found 507.282.

To a stirred solution of 2-methyl-2-((prop-2-yn-1-yloxy)carbonyl)propane-1,3-diyl bis(2,2,5-trimethyl-1,3-dioxane-5-carboxylate), 23 (15.0 g, 31.0 mmol) in MeOH was added DOWEX resin (10 g) and the resulting suspension stirred at 40° C. for 2 h, after which $^{13}$C NMR showed the disappearance of acetonide quaternary carbon signal (~98 ppm). The suspension was filtered and the filtrate concentrated under reduced pressure to afford compound, 8 (12.46 g, >99%). $^1$H NMR ($CDCl_3$) δ 4.74 (d, J=2.4 Hz, 2H), 4.45 (d, J=11.1 Hz, 2H), 4.29 (d, J=11.2 Hz, 2H), 3.84 (dd, J=10.3, 7.6 Hz, 4H), 3.70 (dd, J=11.4, 9.9 Hz, 4H), 2.71 (s, 4H), 2.49 (t, J=2.4 Hz, 1H), 1.33 (s, 3H), 1.05 (s, 6H); $^{13}$C NMR ($CDCl_3$) δ 175.09, 172.33, 77.36, 75.66, 66.97, 66.95, 64.80, 52.86, 49.90, 46.48, 18.04, 17.21; MALDI-TOF (m/z): [M+Na]$^+$ calcd. for $C_{18}H_{28}O_{10}Na$, 427.1580; found 427.275.

To a stirred solution of compound 8, DMAP and pyridine in $CH_2Cl_2$ (50 mL) was added stearic anhydride and the resulting mixture stirred for 12 h. The reaction mixture was diluted with additional $CH_2Cl_2$ (50 mL), washed with 1N HCl (3×50 mL), dried over anhydrous $MgSO_4$, filtered and filtrate concentrated under reduced pressure. The residue was purified by column chromatography ($SiC_2$, 0-50% EtOAc:hexanes) to afford compound 13 (6.1 g, 88%). Compound 13 was further purified by repeated precipitation from $CHCl_3$/MeOH). $^1$H NMR (500 MHz, $CDCl_3$) δ 4.71 (d, J=2.4 Hz, 2H), 4.28 (d, J=11.1 Hz, 2H), 4.24 (d, J=11.1 Hz, 2H), 4.22-4.12 (m, 8H), 2.50 (t, J=2.0 Hz, 1H), 2.28 (t, J=7.6 Hz, 8H), 1.62-1.54 (m, 8H), 1.31-1.23 (m, 115H), 1.22 (s, 6H), 0.87 (t, J=6.7 Hz, 12H); $^{13}$C NMR ($CDCl_3$) δ 173.33, 172.20, 171.56, 77.21, 75.67, 65.75, 65.14, 52.90, 46.81, 46.56, 34.18, 32.08, 29.86, 29.83, 29.81, 29.79, 29.65, 29.51, 29.44, 29.29, 25.01, 22.84, 17.93, 17.60, 14.26; MALDI-TOF (m/z): [M+Na]$^+$ calcd. for $C_{90}H_{164}O_{14}Na$, 1492.2019; found 1491.808.

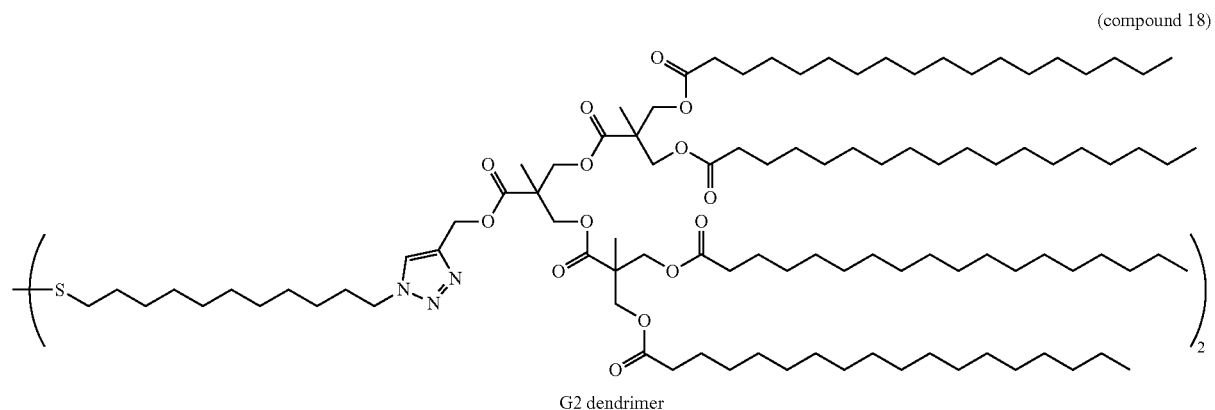

(compound 18)

G2 dendrimer

The G2 dendrimer (compound 18) was formed by coupling compound 4 and compound 13 under conditions used to couple compound 4 and compound 12 in Example 1, affording 18 as a white solid (0.82 g, 83%). $^1$H NMR ($CDCl_3$) δ 7.67 (s, 2H), 5.24 (s, 4H), 4.35 (t, J=7.3 Hz, 4H), 4.25 (d, J=11.1 Hz, 4H), 4.21 (d, J=11.0 Hz, 4H), 4.18-4.08 (m, 16H), 2.66 (t, J=7.3 Hz, 4H), 2.28 (t, J=7.6 Hz, 16H), 1.95-1.86 (m, 4H), 1.70-1.62 (m, 4H), 1.61-1.53 (m, 16H), 1.37-1.24 (m, 252H), 1.22 (s, 6H), 1.17 (s, 12H), 0.87 (t, J=6.9 Hz, 24H); $^{13}$C NMR ($CDCl_3$) δ 173.34, 172.13, 142.07, 124.18, 65.66, 65.08, 58.62, 50.54, 46.79, 46.48, 39.21, 34.16, 32.07, 30.45, 29.86, 29.83, 29.81, 29.79, 29.66, 29.64, 29.57, 29.51, 29.45, 29.41, 29.35, 29.29, 29.19, 28.68, 26.69, 25.01, 22.83, 17.90, 17.65, 14.26; MALDI-TOF (m/z): [M+Na]$^+$ calcd. for $C_{202}H_{372}N_6O_{28}S_2Na$, 3417.7209; found 3417.712.

Example 3. Synthesis of G3 Dendrimer (Compound 19)

Compound 14 was initially synthesized according to Scheme 4 below.

Scheme 4
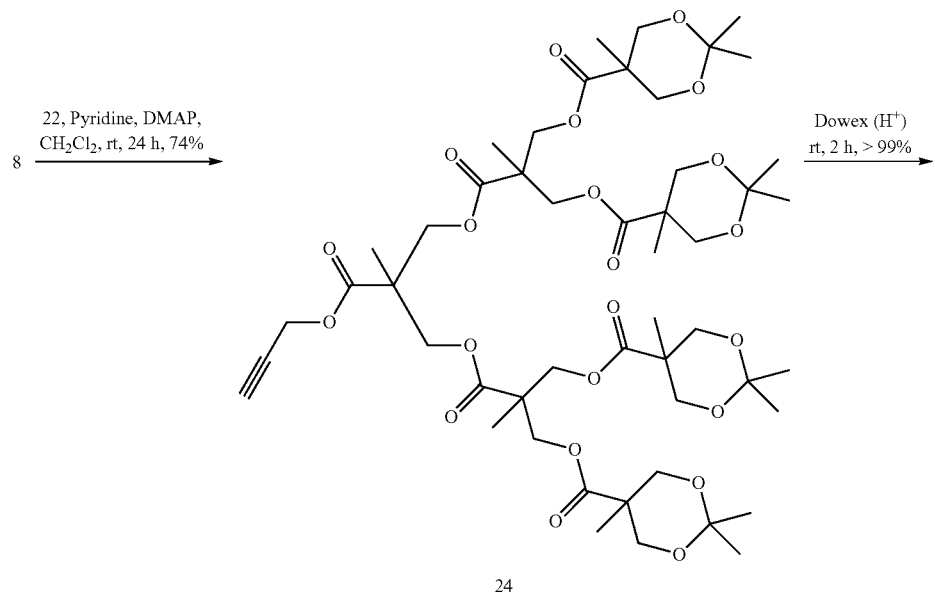
24
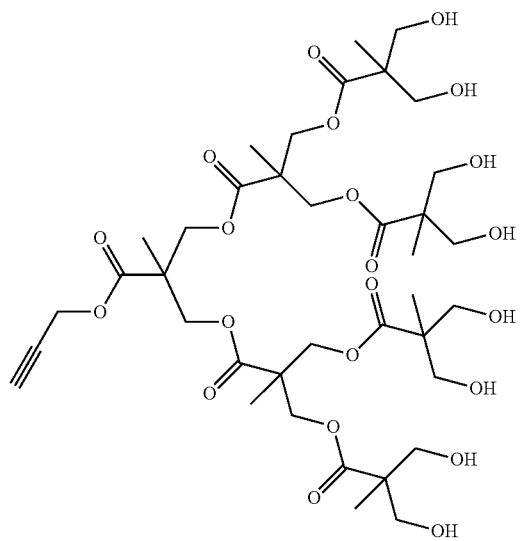
9

-continued
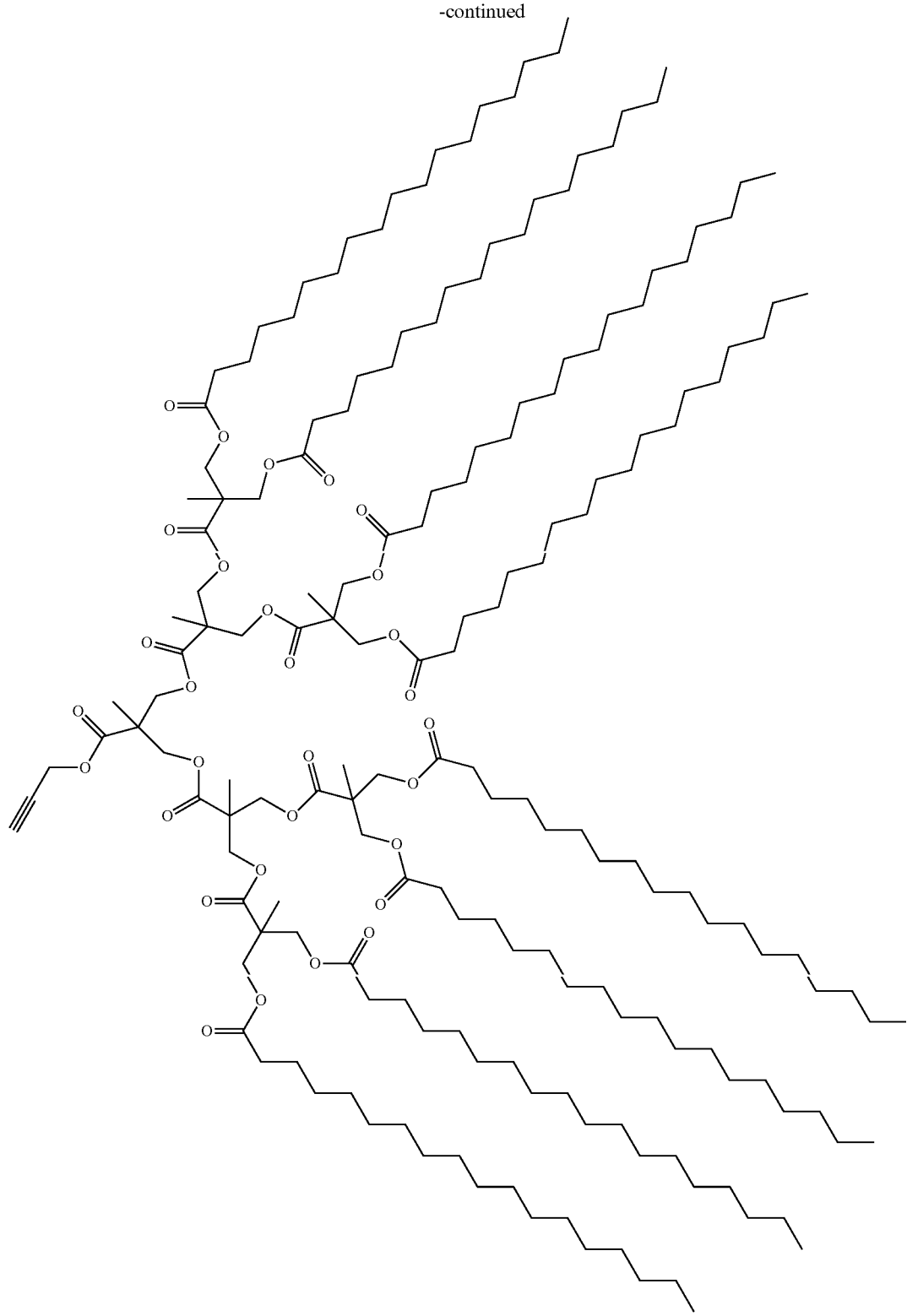
14
Compound 24 was synthesized according to the procedure decribed in Example 2, except that compound 8 was used instead of compound 7. 5.8 g of compound 24 was obtained (74%). $^1$H NMR (CDCl$_3$) δ 4.73 (d, J=2.4 Hz, 2H), 4.34- 4.26 (m, 10H), 4.22 (d, J=11.1 Hz, 2H), 4.13 (d, J=12.0 Hz, 8H), 3.61 (d, J=13.2 Hz, 8H), 2.53 (t, J=2.5 Hz, 1H), 1.40 (s, 12H), 1.34 (s, 12H), 1.29 (s, 3H), 1.27 (s, 6H), 1.13 (s, 12H); $^{13}$C NMR (CDCl$_3$) δ 173.61, 171.96, 171.51, 98.23, 77.27, 75.82, 66.10, 66.06, 65.08, 52.97, 47.02, 46.80, 42.18, 25.38, 22.11, 18.63, 17.79, 17.65; MALDI-TOF (m/z): [M+Na]$^+$ calcd. for $C_{50}H_{76}O_{22}Na$, 1051.4726; found 1051.341.

Compound 9 was synthesized from compound 24 under conditions described for the conversion of compound 23 to compound 8 in Example 2. 4.2 g of compound 9 was obtained (>99%). $^1$H NMR (CDCl$_3$) δ 4.79 (d, J=2.5 Hz, 2H), 4.37-4.22 (m, 12H), 3.67 (dd, J=10.9, 2.9 Hz, 8H), 3.60 (d, J=10.9 Hz, 8H), 2.99 (t, J=2.5 Hz, 1H), 1.32 (s, 3H), 1.30 (s, 6H), 1.15 (s, 12H); $^{13}$C NMR (CDCl$_3$) δ 175.78, 173.62, 173.04, 78.48, 77.00, 67.12, 66.07, 65.73, 53.69, 51.65, 49.85, 47.83, 18.18, 17.92, 17.25.

Compound 14 was synthesized from compound 9 under conditions described for the conversion of compound 8 to compound 13. 4.04 g of compound 14 (89%) was obtained. $^1$H NMR (CDCl$_3$) δ 4.72 (d, J=2.5 Hz, 2H), 4.29 (d, J=11.1 Hz, 2H), 4.25-4.12 (m, 24H), 2.51 (t, J=2.1 Hz, 1H), 2.27 (t, J=7.6 Hz, 16H), 1.64-1.50 (m, 16H), 1.32-1.21 (m, 233H), 1.21 (s, 12H), 0.86 (t, J=6.8 Hz, 24H); $^{13}$C NMR (CDCl$_3$) δ 173.26, 172.14, 171.56, 171.41, 77.36, 75.74, 66.33, 65.36, 65.02, 52.94, 46.85, 46.77, 46.50, 34.15, 32.07, 29.86, 29.84, 29.81, 29.67, 29.51, 29.46, 29.30, 25.00, 22.83, 17.93, 17.64, 17.56, 14.25; MALDI-TOF (m/z): [M+Na]$^+$ calcd. for $C_{182}H_{332}O_{30}Na$, 3021.4351; found 3021.622.

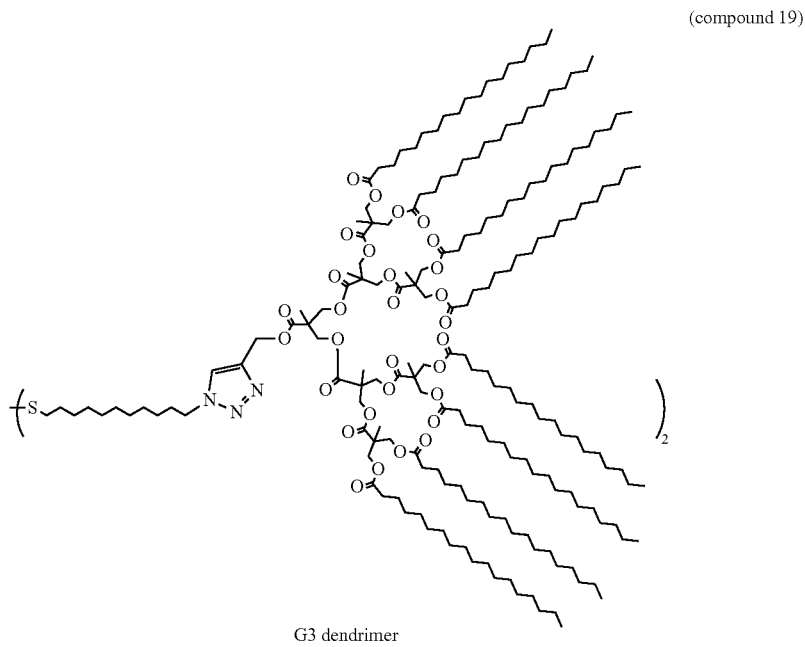

(compound 19)

G3 dendrimer

To form the G3 dendrimer (compound 19), compound 14 was coupled with compound 4 under conditions similar to those used to couple compound 4 and compound 12 in Example 1. Instead of stirring for 2 h under microwave irradiation, the reactants were stirred for 3 h under microwave irradiation. Compound 14 was obtained as a white solid (0.71 g, 71%). $^1$H NMR (CDCl$_3$) δ 7.69 (s, 2H), 5.24 (s, 4H), 4.33 (t, J=7.3 Hz, 4H), 4.29-4.09 (m, 56H), 2.65 (t, J=7.2 Hz, 4H), 2.27 (t, J=7.6 Hz, 32H), 1.94-1.84 (m, 4H), 1.69-1.61 (m, 4H), 1.61-1.51 (m, 32H), 1.38-1.215 (m, 476H), 1.12 (s, 32H), 1.18 (s, 12H), 0.86 (t, J=6.6 Hz, 11H), $^{13}$C NMR (CDCl$_3$) δ 173.24, 172.15, 172.10, 171.52, 141.97, 124.12, 66.22, 65.31, 64.99, 58.69, 50.51, 46.78, 46.71, 46.48, 39.14, 34.13, 32.05, 30.49, 29.84, 29.82, 29.79, 29.66, 29.60, 29.49, 29.45, 29.43, 29.34, 29.29, 29.21, 28.69, 26.70, 24.99, 22.81, 17.90, 17.59, 17.56, 14.23; MALDI-TOF (m/z): [M+Na]$^+$ calcd. for $C_{386}H_{708}N_6O_{60}S_2Na$, 6476.1874; found 6479.136.

Example 4. Synthesis of G4 Dendrimer (Compound 20)
Compound 15 was synthesized according to Scheme 5 below.
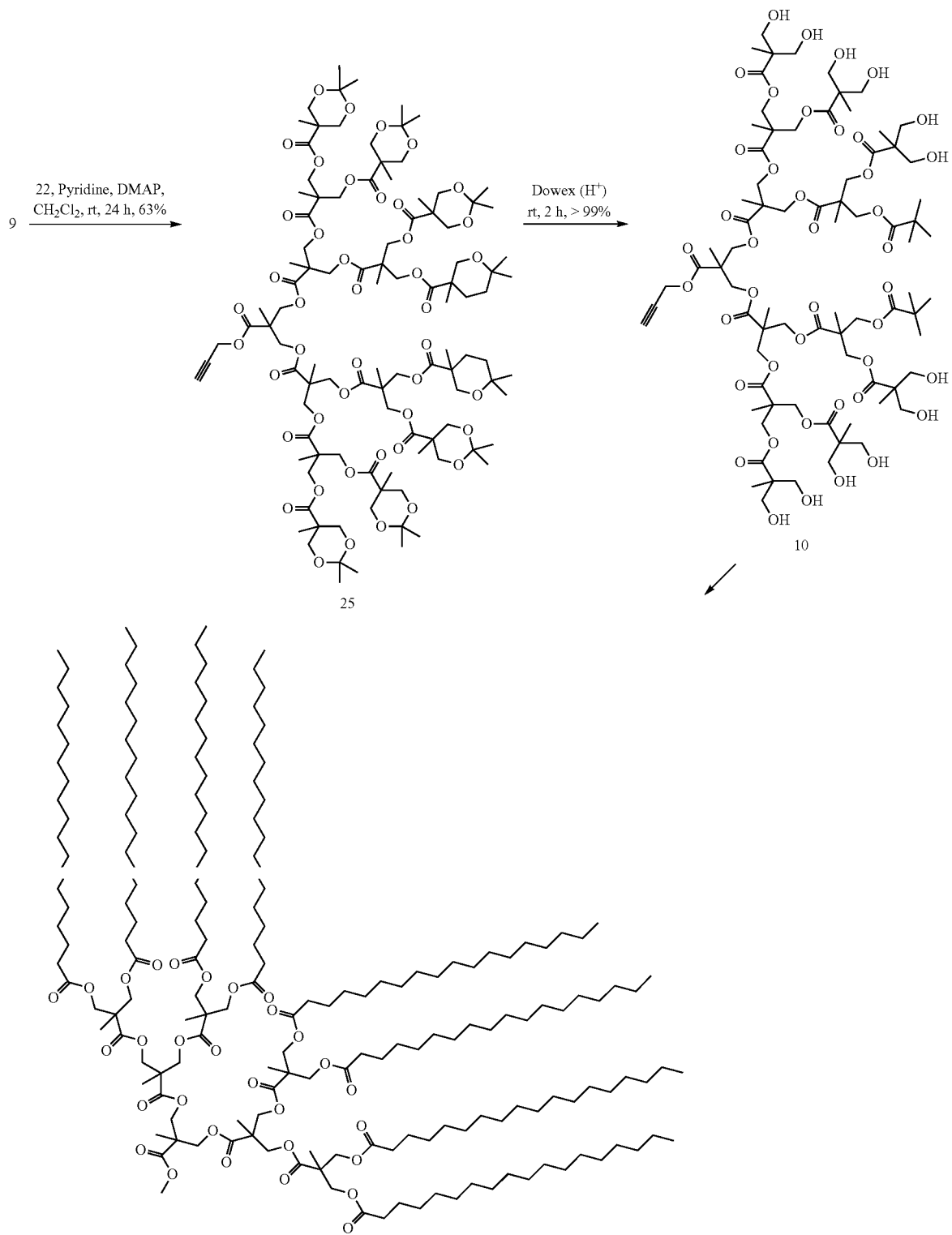

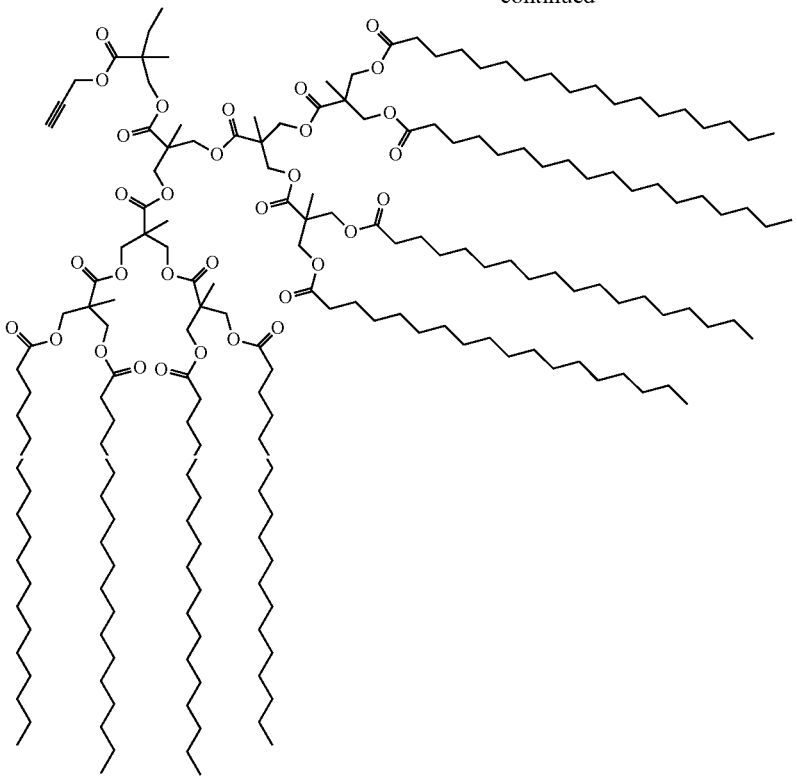

15

Compound 25 was synthesized according to the procedure decribed in Example 2, except that compound 9 was used instead of compound 7. (0.93 g, 63%). $^1$H NMR (CDCl$_3$) δ 4.70 (d, J=2.3 Hz, 2H), 4.32-4.17 (m, 28H), 4.11 (d, J=11.7 Hz, 16H), 3.58 (d, J=12.0 Hz, 16H), 2.55 (t, J=2.4 Hz, 1H), 1.38 (s, 24H), 1.31 (s, 24H), 1.28 (s, 3H), 1.24 (s, 12H), 1.23 (s, 6H), 1.11 (s, 24H); $^{13}$C NMR (CDCl$_3$) δ 173.53, 171.88, 171.46, 171.33, 98.15, 77.35, 75.90, 66.44, 66.03, 65.97, 65.64, 64.91, 52.93, 46.91, 46.80, 46.77, 42.10, 25.26, 22.14, 18.58, 17.75, 17.57, 17.49; MALDI-TOF (m/z): [M+Na]$^+$ calcd. for C$_{102}$H$_{156}$O$_{46}$Na, 2139.9765; found 2139.537.

Compound 10 was synthesized from compound 25 under conditions described for the conversion of compound 23 to compound 8 in Example 2. (0.55 g, >99%) $^1$H NMR (CD$_3$OD) δ 4.80 (d, J=2.5 Hz, 2H), 4.39-4.28 (m, 20H), 4.25 (d, J=10.5 Hz, 8H), 3.67 (dd, J=10.9, 2.8 Hz, 16H), 3.60 (d, J=10.9 Hz, 16H), 3.00 (t, J=2.4 Hz, 1H), 1.35 (s, 3H), 1.32 (s, 6H), 1.30 (s, 12H), 1.15 (s, 24H); $^{13}$C NMR (CD$_3$OD) δ 175.81, 173.67, 173.17, 173.00, 78.60, 77.11, 67.40, 66.99, 66.07, 65.74, 53.79, 51.68, 47.98, 47.86, 47.82, 18.25, 18.03, 17.97, 17.29; MALDI-TOF (m/z): [M+Na]$^+$ calcd. for C$_{78}$H$_{124}$O$_{46}$Na, 1819.7261; found 1819.407.

Compound 15 was synthesized from compound 10 under conditions described for the conversion of compound 8 to compound 13. (0.7 g, 74%). White solid. MP=41.6° C. $^1$H NMR (CDCl$_3$) δ 4.72 (d, J=2.4 Hz, 2H), 4.38-4.07 (m, 60H), 2.59 (t, J=2.5 Hz, 1H), 2.27 (t, J=7.6 Hz, 32H), 1.57 (t, J=7.3 Hz, 32H), 1.33-1.22 (m, 469H), 1.21 (s, 24H), 0.87 (t, J=6.8 Hz, 48H); $^{13}$C NMR (CDCl$_3$) δ 173.22, 172.12, 171.57, 171.44, 171.36, 77.36, 75.97, 66.80, 65.75, 65.17, 64.93, 53.02, 46.92, 46.79, 46.62, 46.46, 34.14, 32.08, 29.89, 29.87, 29.84, 29.82, 29.70, 29.52, 29.50, 29.33, 25.01, 22.84, 17.95, 17.66, 17.57, 17.48, 14.25; MALDI-TOF (m/z): [M+Na]$^+$ calcd. for C$_{366}$H$_{668}$O$_{62}$Na, 6079.9016; found 6081.758.

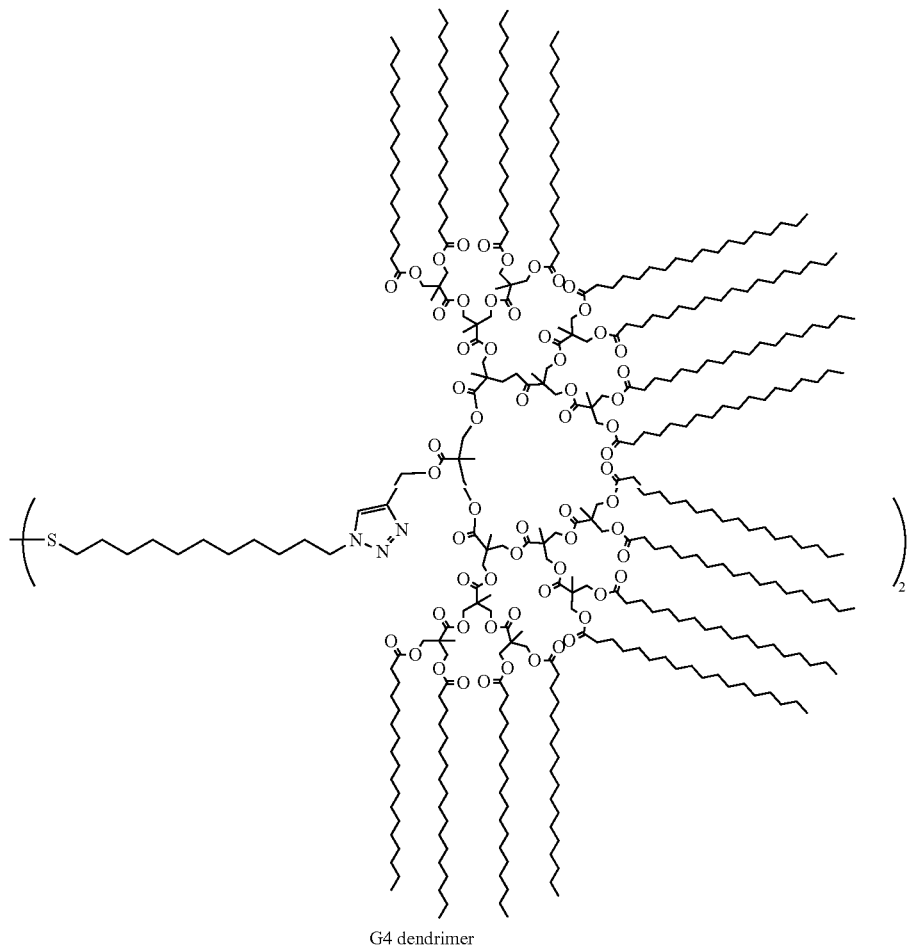

G4 dendrimer (compound 20)

To form the G4 dendrimer (compound 20), compound 15 was coupled with compound 4 under conditions similar to those used to couple compound 4 and compound 12 in Example 1. Instead of stirring for 2 h under microwave irradiation, the reactants were stirred for 6 h under microwave irradiation. White solid (0.2 g, 52%). $^1$H NMR (CDCl$_3$) δ 7.72 (s, 2H), 5.23 (s, 4H), 4.35 (t, J=7.4 Hz, 4H), 4.31-4.12 (m, 120H), 2.66 (t, J=7.3 Hz, 4H), 2.28 (t, J=7.6 Hz, 64H), 1.96-1.85 (m, 4H), 1.69-1.63 (m, 4H), 1.59-1.55 (m, 64H), 1.31-1.23 (m, 966H), 1.21 (s, 48H), 0.88 (t, J=6.9 Hz, 96H); $^{13}$C NMR (CDCl$_3$) δ 173.23, 172.15, 172.08, 171.61, 171.45, 141.91, 124.21, 66.67, 65.74, 65.17, 64.95, 46.89, 46.81, 46.76, 46.49, 39.07, 36.88, 34.17, 34.17, 32.09, 29.91, 29.90, 29.87, 29.84, 29.73, 29.62, 29.54, 29.35, 28.85, 26.86, 25.04, 22.85, 17.98, 17.68, 17.58, 17.53, 14.27; MALDI-TOF (m/z): [M+Na]$^+$ calcd. for C$_{754}$H$_{1380}$N$_6$O$_{124}$S$_2$Na, 12593.1203; found 12594.357.

Example 5. Synthesis of the G0 Dendrimer (Compound 16)

The G0 dendrimer (compound 16) was synthesized according to Scheme 6 below.

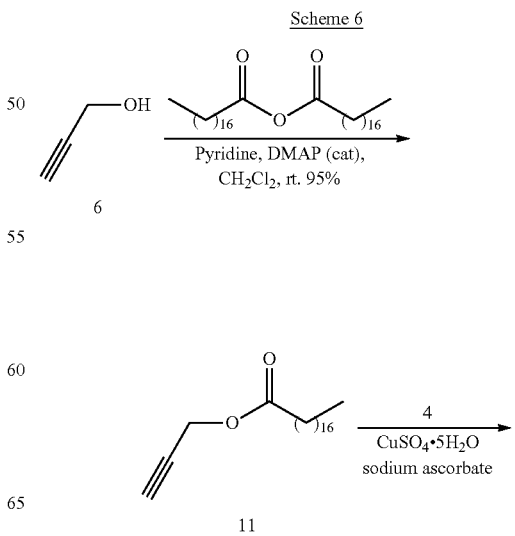

Scheme 6

-continued

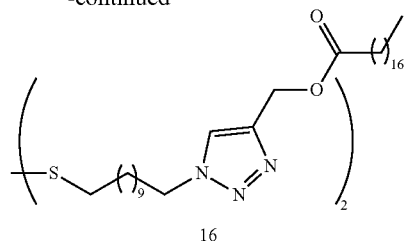

16

To a stirred solution of propargyl alcohol 6 (1 g, 17.8 mmol), DMAP (0.22 g, 1.8 mmol) and pyridine (2.8 g, 35.6 mmol) in $CH_2Cl_2$ (50 mL) was added stearic anhydride (11.8 g, 21.4 mmol) and the resulting mixture stirred for 12 h. The reaction mixture was diluted with additional $CH_2Cl_2$ (50 mL), washed with 1N HCl (3×50 mL), dried over anhydrous $MgSO_4$, filtered and filtrate concentrated under reduced pressure. The residue was purified by column chromatography ($SiO_2$, 0-50% EtOAc:hexanes) to afford compound 11 (5.46 g, 95%). $^1H$ NMR ($CDCl_3$) δ 4.67 (d, J=2.5 Hz, 2H), 2.46 (t, J=2.5 Hz, 1H), 2.34 (t, J=7.5 Hz, 2H), 1.63 (p, J=7.3 Hz, 2H), 1.33-1.23 (m, 28H), 0.87 (t, J=6.9 Hz, 3H); $^{13}C$ NMR ($CDCl_3$) δ 173.10, 77.94, 74.80, 51.86, 34.13, 32.07, 29.84, 29.82, 29.80, 29.78, 29.72, 29.57, 29.50, 29.36, 29.20, 24.95, 22.83, 14.25.

To a stirred solution of prop-2-yn-1-yl stearate, 11 (2 g, 6.2 mmol), 1,2-bis(11-azidoundecyl)disulfane, 4 (1.42 g, 3.1 mmol) and $CuSO_4.5H_2O$ (0.3 g, 1.24 mmol) in $THF/H_2O$ 4:1 (10 mL) was added sodium ascorbate (0.49 g, 2.48 mmol) and the resulting mixture stirred at 60° C. for 2 h under microwave irradiation (constant temperature mode). The solvent was evaporated, residue was dissolved in $CHCl_3$ (100 mL) and washed with 1N HCl (3×20 mL). The organic layer was dried over anhydrous $Na_2SO_4$, filtered and the filtrate concentrated under reduced pressure.

The crude product was purified by column chromatography ($SiO_2$, 0-100% EtOAc:hexanes) to afford compound 16 (3.14 g, 92%). White solid. mp=114.8° C. $^1H$ NMR ($CDCl_3$) δ 7.67 (s, 2H), 5.21 (s, 4H), 4.35 (t, J=6.8 Hz, 4H), 2.68 (t, J=7.3 Hz, 4H), 2.32 (t, J=7.4 Hz, 4H), 1.96-1.86 (m, 4H), 1.72-1.54 (m, 8H), 1.40-1.22 (m, 80H), 0.88 (t, J=6.9 Hz, 6H); $^{13}C$ NMR ($CDCl_3$) δ 173.83, 57.66, 53.51, 50.79, 39.40, 34.34, 32.07, 30.34, 29.84, 29.82, 29.79, 29.74, 29.60, 29.57, 29.49, 29.38, 29.35, 29.28, 29.11, 28.66, 26.68, 25.04, 22.82, 14.21; MALDI-TOF (m/z): $[M+Na]^+$ calcd. for $C_{64}H_{120}N_6O_4S_2Na$, 1123.8710; found 1123.333.

Example 6. Synthesis and Characterization of Hybrid Nanoparticles

Synthesis of gold nanoparticles, capped with oleylamine, was performed according to a published procedure (see Peng, S.; Lee, Y.; Wang, C.; Yin, H.; Dai, S.; Sun, S. *Nano Res.* 2008, 1, 229). 200 mg of $HAuCl_4.3H_2O$ were dissolved in 20 mL of oleylamine and 20 mL of tetralin. 1 mmol of TBAB dissolved in 2 mL of oleylamine and 2 mL of tetralin was then quickly injected into the stirring gold solution. The mixture was left stirring open to the atmosphere for one hour. The NPs were precipitated with isopropanol and centrifuged. The solid pellet of NPs was redispersed in hexanes. The NPs were washed twice with isopropanol before finally being redispersed in 20 mL of hexane.

Ligand exchange of the oleylamine-capped Au NPs (designated Au@OLAM) using the dendrimers synthesized according to Examples 1-5 was performed using 1 mL of Au NPs in hexanes at 5 mg/mL added to 5 mL of chloroform in which was dissolved 5 mg of the disulfide dendrimer. Each reaction was stirred for 20 minutes at room temperature, then the reaction was stopped by precipitation of the NPs with ethanol. After centrifugation, the solid pellet of NPs was redispersed in hexanes and precipitated a second time with a mixture of isopropanol and ethanol. The resulting hybrid nanoparticles were designated Au@L, where L represents a ligand derived from the dendrimers made in Examples 1-5.

For comparison, NPs having a commercially-available ligand (DDT) was made. NPs having DDT (designated Au@DDT) were made according to a similar procedure, wherein 10 μL of the thiol was dissolved in the chloroform solution instead of the inventive dendrimer.

The presence of the dendrons on the NP surface and the effect on interparticle spacing were confirmed by a combination of techniques including NMR and UV-Vis spectroscopies, thermogravimetric analysis (TGA), transmission electron microscopy (TEM) and small-angle X-ray scattering (SAXS). Unambiguous results were obtained when solution phase NMR spectroscopy was used.

Thermogravimetric analysis (TGA) was carried out using a TA Instruments TGA Q600 apparatus in the temperature range of 25° C. to 500° C. under $N_2$ flow at a heating rate of 30° C./min. Thermal transitions were determined on a TA Instruments Q2000 differential scanning calorimeter (DSC) equipped with a liquid nitrogen cooling system with 10° C./min heating and cooling rates.

Small-angle transmission X-ray scattering (SAXS) was performed using a Multi-angle X-ray scattering instrument equipped with a Bruker Nonius FR591 40 kV rotating anode generator operated at 85 mA, Osmic Max-Flux optics, 2D Hi-Star Wire detector, and pinhole collimation, with an evacuated beam path. Measurements were performed on thin glass coverslips (0.1 mm) and collected for roughly 2 hours. Samples were prepared by dropcasting colloidal solutions which were allowed to dry slowly in a partially enclosed chamber. The same samples were used for solid-state UV-Vis experiments.

Figure 2:
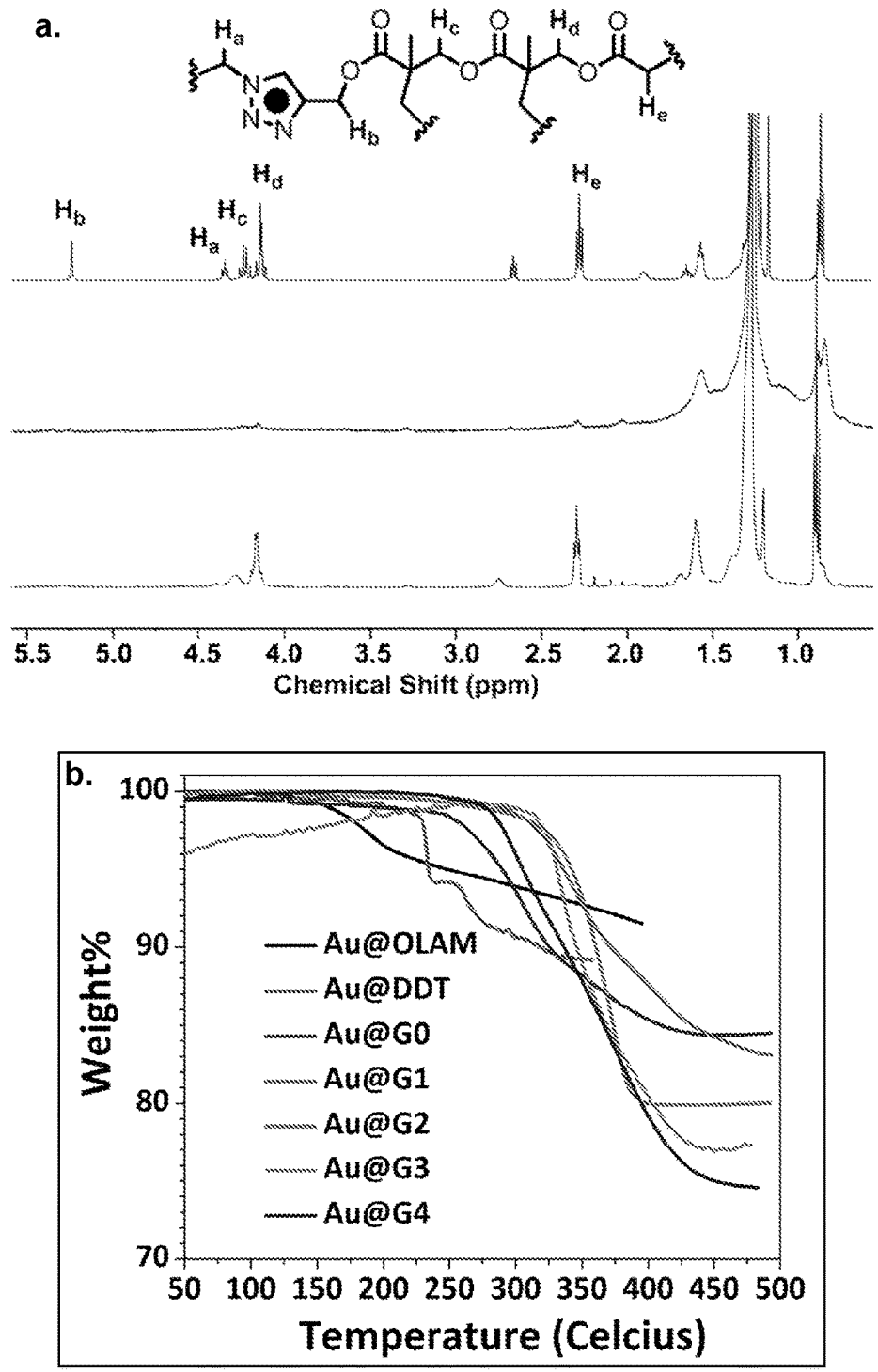
FIG. 2 shows (a) $^1$H NMR spectra (CDCl$_3$, 500 MHz) of free disulfide G2 (top), Au@G2 (middle) and disulfide G2 dendron after iodine treatment of Au@G2 (bottom); and (b) TGA curves for the Au@L hybrid nanoparticles of the present disclosure.

Optical extinction spectra were collected using a Cary 5000 UV-VIS-NIR, for solid films. Spectral band-pass was set to 2 nm and integration time to 0.25 seconds. Solution-phase measurements were collected on an Analytical Spectral Devices QSP 350-2000 UV-VIS-NIR spectrometer. $^1H$ NMR spectroscopy demonstrating ligand exchange is shown in FIG. 2a. In addition to aliphatic protons several spectral resonances of the free dendritic ligand (G2 in this case) can be assigned as shown. Once ligand exchange has proceeded, a substantial broadening of the representative proton signals of the dendrons was observed, to such an extent that some resonances were no longer distinguishable from the baseline. This phenomenon essentially accounts for the hindered and slower dynamics of the dendrons bound to the NP with respect to those of the free ligands, the time scale of the NMR presenting an average of all possible conformations. Furthermore, when the sample in solution was treated with iodine, the thiol-containing dendritic ligands were oxidized off of the Au NP surface, as NMR shows that the specific signals from the ligand are mostly recovered after iodine oxidation. Albeit destructive, this method provides an unambiguous proof of the presence of dendritic ligands on the Au NP surfaces.

The plasmonic and structural properties of the inventive hybrid nanoparticles are summarized in Tables 1 and 2 below.

TABLE 1*

| L (Au@L) | $\lambda_{max}$/nm | q/nm$^{-1}$ | d/nm | a/nm | s/nm | MW/g mol$^{-1}$ |
|---|---|---|---|---|---|---|
| DDT | 575 | 0.825 | 7.6 | 8.0 | 2.2 | 202.4 |
| G0 | 554 | 0.715 | 8.8 | 9.2 | 3.4 | 551.9 |
| G1 | 535 | 0.685 | 9.2 | 9.6 | 3.8 | 934.5 |
| G2 | 534 | 0.605 | 10.4 | 10.9 | 5.1 | 1699.7 |
| G3 | 531 | 0.595 | 10.6 | 11.1 | 5.3 | 3230.0 |

TABLE 1*-continued

| L (Au@L) | $\lambda_{max}$/nm | q/nm$^{-1}$ | d/nm | a/nm | s/nm | MW/g mol$^{-1}$ |
|---|---|---|---|---|---|---|
| G4 | 528 | 0.545 | 11.5 | 12.1 | 6.3 | 6290.7 |
| OLAM | — | — | — | — | — | 267.5 |

*L: ligand type on the NP surface (G0-G4 are inventive thiol-containing dendrons); $\lambda_{max}$: maximum of the absorption wave-length in solid films; q: q-vector, d = $2\pi/q$, diffraction spacing; a = $[3dLog3]/\pi$, average interparticular distance; s = a − Φ, edge-to-edge separation, from SAXS (Φ = 5.8 nm, NP diameter); MW: ligand molecular weight; wt %: weight fraction of ligands, from TGA.

TABLE 2**

| L (Au@L) | wt % | $n_L$ | f | $\Phi_{hyb}$/nm | s'/nm | δ/L nm$^{-2}$ | σ/Å$^3$ |
|---|---|---|---|---|---|---|---|
| DDT | 7.4 | 469 | 64.5 | 8.2 | 2.4 | 4.5 | 22.2 |
| G0 | 14.7 | 371 | 78.7 | 9.7 | 3.9 | 3.5 | 28.6 |
| G1 | 16.9 | 259 | 81.3 | 10.2 | 4.4 | 2.5 | 40.0 |
| G2 | 20.0 | 175 | 84.3 | 10.8 | 5.0 | 1.6 | 60.6 |
| G3 | 21.0 | 98 | 85.1 | 11.0 | 5.1 | 0.9 | 111.1 |
| G4 | 28.0 | 73 | 89.3 | 12.2 | 6.4 | 0.7 | 142.8 |
| OLAM | 9.0 | 440 | 70.2 | 8.6 | 2.9 | 4.2 | 23.8 |

**$n_L$ = {wt % (L)/[1 − wt %(L)]} · [MW$_{Au@NP}$/MW$_L$], number of (thiol) ligands grafted on the NP surface; MW$_{Au@NP}$ = $n_{Au}$ · MW$_{Au}$ = 1.19 × 10$^6$ g mol$^{-1}$, molecular weight of NP; MW$_{Au}$ = 196.967 g mol$^{-1}$; V$_{Au@NP}$ = $4\pi(\Phi/2)^3/3$ = 102.2 nm$^3$, NP volume; V$_{Au}$ = 16.923 Å$^3$; $n_{Au}$ = V$_{Au@NP}$/V$_{Au}$ = 6036-6037, number of Au atoms in NP; f = $n_L V_L/(n_L V_L + V_{Au@NP})$, ligand volume fraction; V$_L$ = $n_L$[MW$_L$/0.6022ρ], volume of the dendritic part estimated assuming a density, ρ = 0.9 g cm$^{-3}$ (for DDT and OLAM, ρ = 0.85 and 0.813 g cm$^{-3}$, respectively); $\Phi_{hyb}$ = $2[(\Phi/2)^3/(1-f)]^{1/3}$, hybrid diameter; s' = $\Phi_{hyb}$ − Φ, edge-to-edge separation, from TGA; δ = $n_L/4\pi(\phi/2)^2$, grafting density; σ = 100/δ, ligand cross-section area.

The organic weight fraction for each sample was obtained by heating under air to 500° C. The TGA curves are shown in FIG. 2b. These measurements showed that essentially all the oleylamine ligands were displaced by the disulfide-containing ligands, which form a stronger bond with gold. A substantial enhancement of the overall thermal stability of the hybrid nanoparticles with respect to the OLAM-precursor and the DDT-capped Au NP (from ca 50 up to 100° C.) was also observed upon increasing the dendritic generation, which suggests that the numerous diverging liphophilic chains are tightly packed in the shell corona and efficiently shield the inorganic core. The volume fractions of the organic parts, directly deduced from the weight fractions and reasonably assuming a density of 0.9 g·cm$^{-3}$ for the dendrons (due to their lipophilic nature and low-temperature solid behavior), allowed estimations of the number of ligands per Au NP, hybrids' radii, and grafting densities. The Au@DDT and Au@OLAM samples showed similar grafting densities, which, as expected, decreased with each new generation, most likely due to steric hindrance. The hybrids' diameters also increase steadily with the size of the dendrons.

Figure 3:
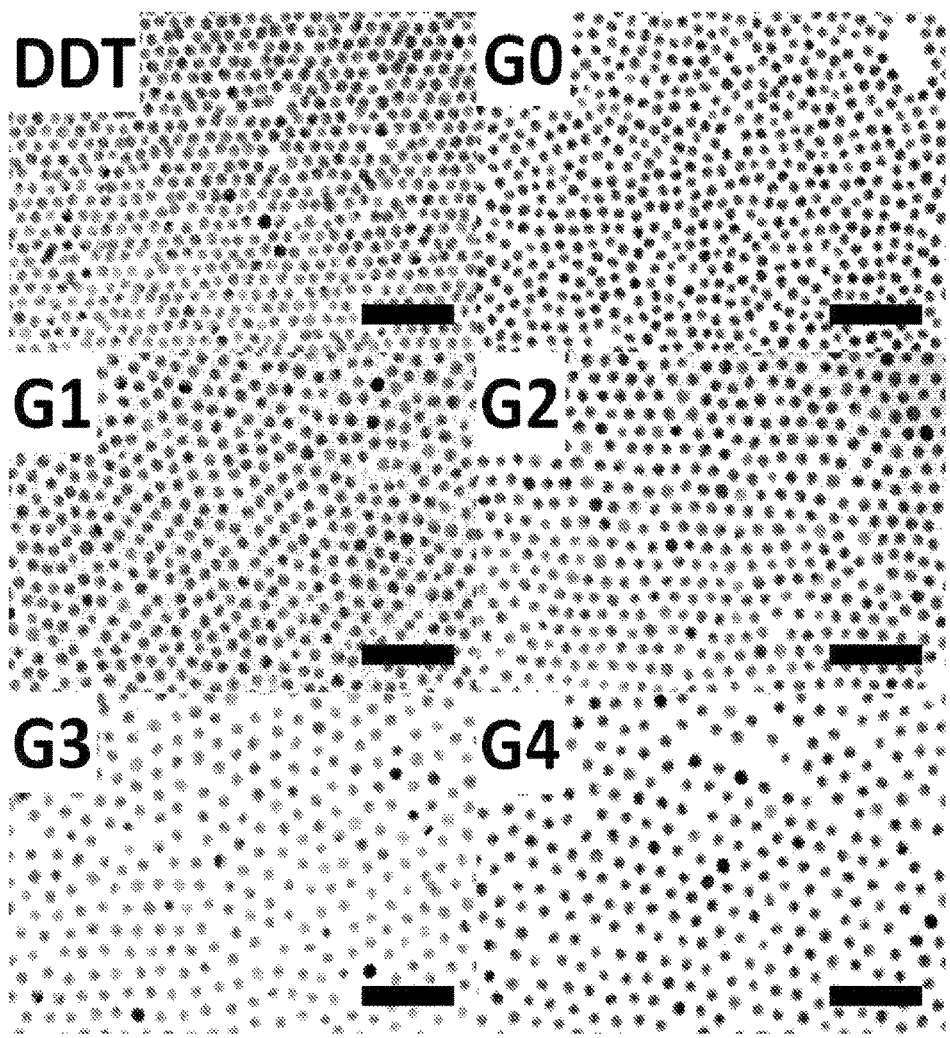
FIG. 3 shows the TEM micrographs of monolayers of Au@DDT and Au@G0-G4. Scale bars are 50 nm.

Example 7. Inventive Films from Dilute Compositions Containing Hybrid Nanoparticles To provide a visual demonstration of the ligand-mediated interparticle spacings, NP monolayer assemblies were obtained by drop-casting dilute hexanes dispersions of the hybrids (<1 mg mL$^{-1}$) onto diethylene glycol liquid surfaces, followed by controlled evaporation. TEM micrographs (collected using a JEOL 1400 microscope operated at 120 kV and calibrated using a MAG*I*CAL® TEM calibration standard) were taken of the monolayer assemblies. FIG. 3 shows the progressive increase of interparticle separation from Au@DDT to Au@G4.

Figure 4:
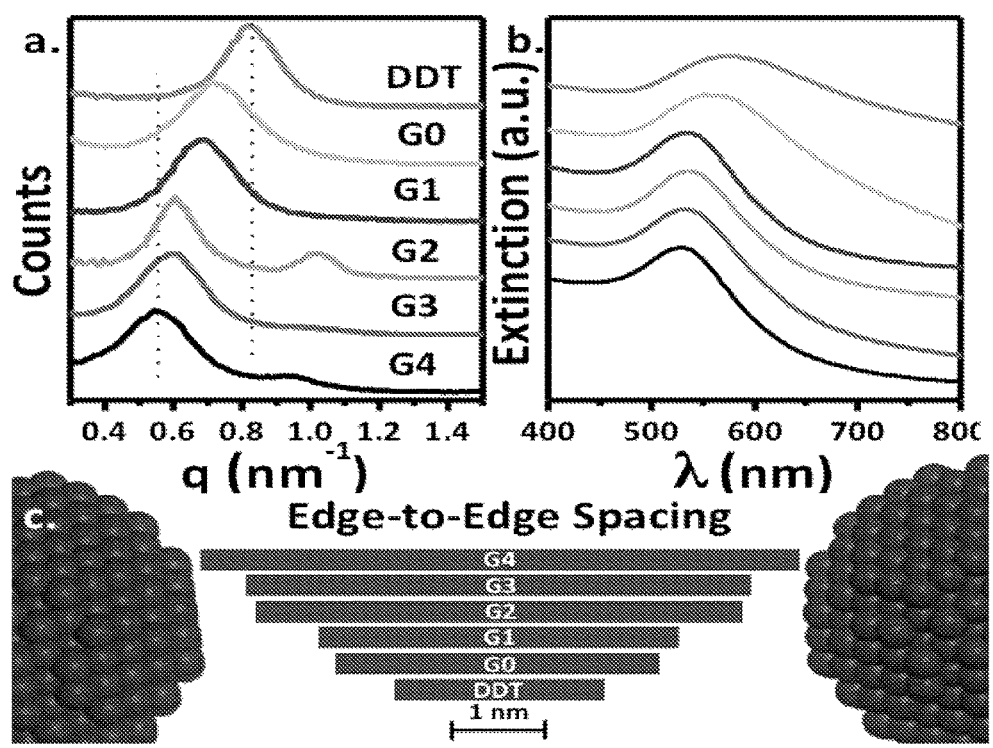
FIG. 4 shows (a) Transmission SAXS of thin solid films composed of Au@L (L=DDT, G0-G4); (b) Extinction spectra of thin solid films composed of Au@L, normalized to the absorption maximum and offset for clarity; and (c) Estimated interparticle edge-to-edge spacings of solids composed of Au@L hybrid nanoparticles of the present disclosure.

SAXS of the films containing the inventive hybrid nanoparticles confirm that the increase in interparticle spacing apparent from the TEM images is replicated throughout drop-cast NP solid films, as shown in FIG. 4a. The maximum of the first peak of the samples shift systematically from a value of q=0.825 nm$^{-1}$ for Au@DDT to q=0.545 nm$^{-1}$ for Au@G4, indicative of an overall increase in separation of approximately 4 nm. Although all the samples are glasses as evidenced by the broadness of the fundamental small-angle reflection, they nevertheless all exhibit short-range hexatic ordering as revealed by TEM images.

Au@G2 and Au@G4 in particular show an additional diffuse reflection, with the center electron density maximum in spacing ratio √3 with respect to first diffraction signal: these two reflections coincide with the first reflections of a hexagonal lattice. It is estimate based upon particle sizing measurements that this corresponds to an edge-to-edge spacing of 2.2 nm for Au@DDT increasing to 6.3 nm for Au@G4, assuming an average hexagonal environment for all the samples. The interparticle distances calculated from TGA data are in very close agreement to the results obtained from X-ray diffraction (comparison of a and $\Phi_{hyb}$, the hybrid diameter, or s and s', see Table 1). This suggests that the soft ligands, and particularly those of smaller generation, deform from a spherical shell to distorted polyhedron in order to more efficiently fill interstices in the solid state.

Figure 5:
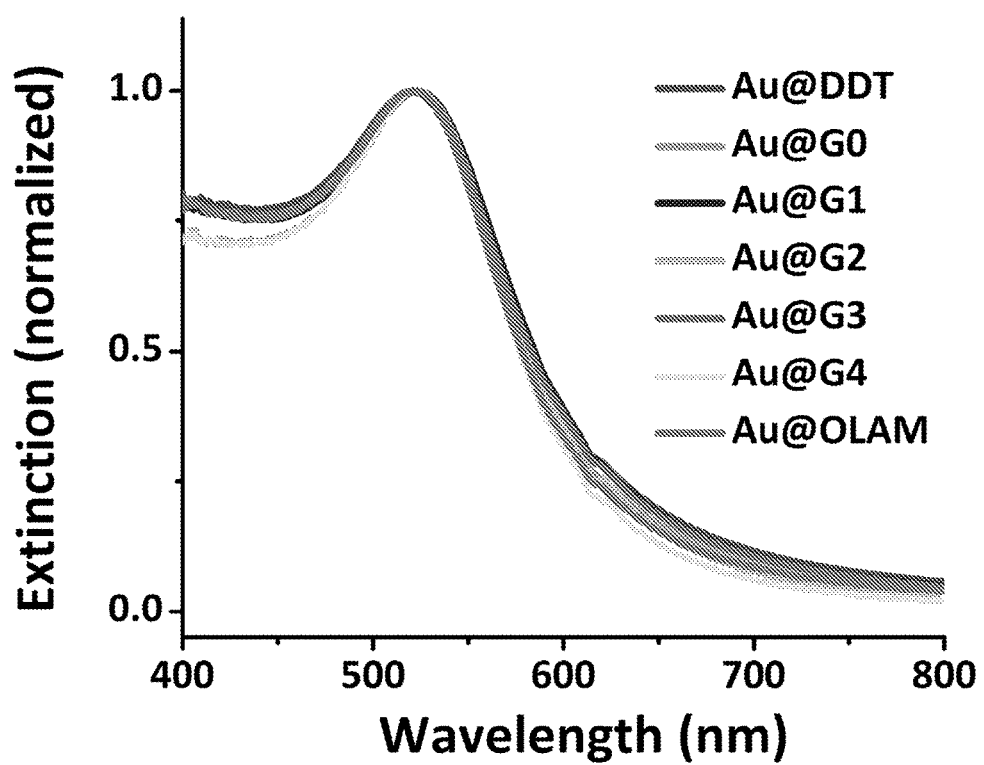
FIG. 5 shows the solution-phase extinction spectra of dispersed Au@L structures in CHCl$_3$ with labels corresponding to the ligand. Absorption maximum $\lambda$=522 nm.

The dramatic change in interparticle spacing is also apparent in the extinction spectra, which as shown in FIG. 4b. In the solution phase, all the samples show nearly superimposable extinction spectra, despite a slight broadening upon increasing generation (see FIG. 5), which indicate that the size and shape uniformity of the particles is preserved through the ligand exchange. When deposited onto thin films, the gold NPs show a redshift and broadening of the visible plasmon resonance compared to the isolated particles. The shift of the plasmon energy from the solution value is largest for Au@DDT and smallest for Au@G4, reflecting the differences in the interparticle spacing within those materials.

Figure 6:
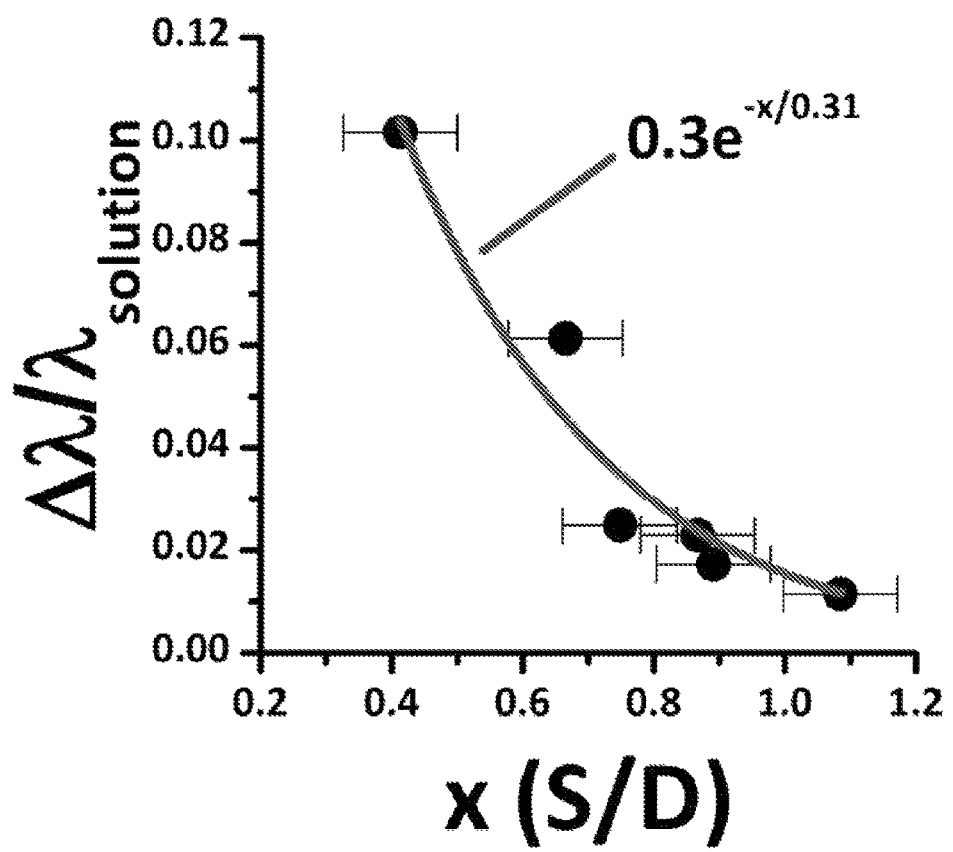
FIG. 6 shows the normalized plasmon shift (y-axis) plotted for the reduced spacing (x-axis, spacing/diameter) as defined in equation 1 described herein. Points mark the reduced spacing with whiskers indicating the standard deviation in size. The fitted curve of the data is shown by the line.

It has been demonstrated that the distance dependence of the absorption properties in pairs of noble metal nanoparticles (normalized to the isolated wavelength as $\Delta\lambda/\lambda_0$) obeys a universal scaling according to equation 1:

$$\Delta\lambda/\lambda_0 = ae^{-x/t} \qquad (1)$$

where x is the is the spacing divided by the diameter (reduced spacing), a and t depending on the interparticle environment and resonator material, respectively (see Jain, P. K.; Huang, W.; El-Sayed, M. A. *Nano Lett.* 2007, 7, 2080). This equation has been empirically verified using lithographically fabricated nanodisk pairs and data from solution-phase measurements of DNA-coupled Au NPs with variable DNA base pair spacings (see Reinhard, B. M.; Siu, M.; Agarwal, H.; Alivisatos, A. P.; Liphardt, *J. Nano Lett.* 2005, 5, 2246). For Au NP pairs, the value of t has been found to range between 0.18-0.27 and the value of a between 0.16-0.29. Fitting our data on interparticle spacing and plasmon shift to equation 1 provides an estimate of t=0.31 and a=0.3 (see FIG. 6), similar to the universal scaling which has been found in previous studies albeit with slightly higher values for both parameters. However, these results were obtained with smaller particles, much smaller absolute spacings than those obtained from DNA-based systems and confirmed in three-dimensional solids rather than small clusters.

Figure 7:
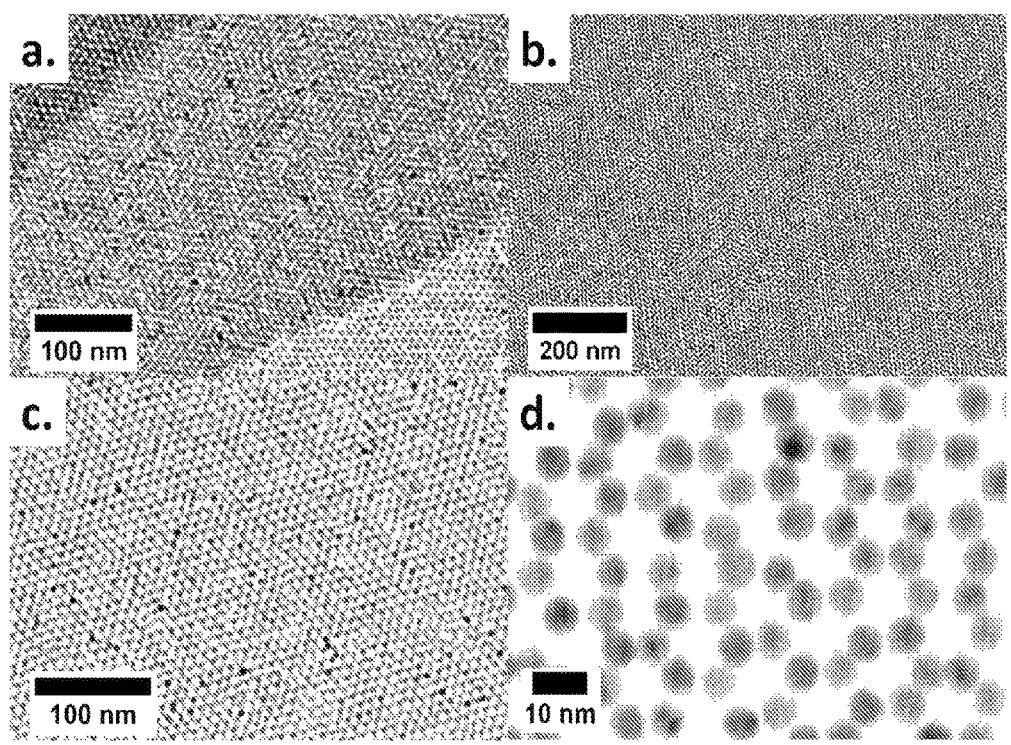
FIG. 7 shows (a) Au@DDT forming monolayer, bilayer, and trilayer in an hcp superlattice film; (b) Multilayer superlattice film of Au@G1 hybrid; (c) Bilayer superlattice film of Au@G2; and (d) High magnification of Au@G4 superlattice bilayer.
Figure 8:
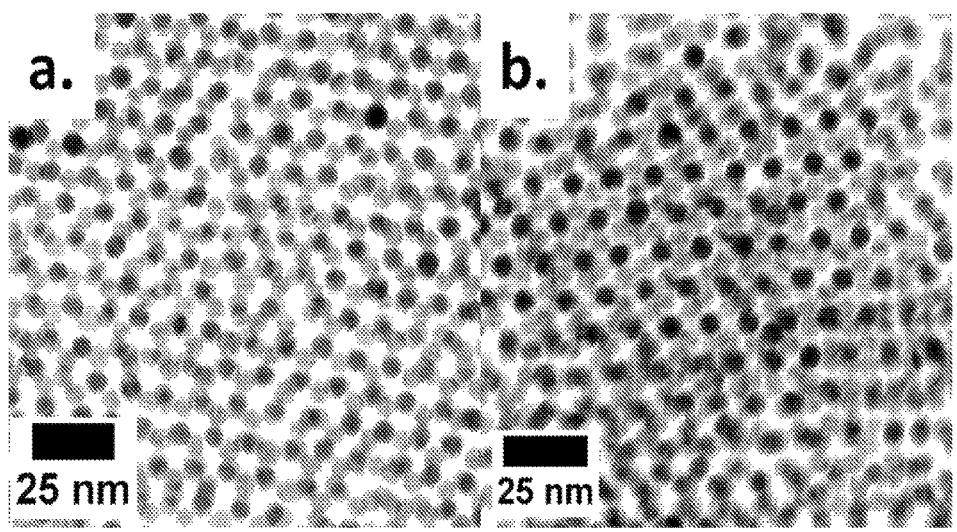
FIG. 8 shows that the [001] projection of hcp structure, depicted in (a), predominates in single-component assemblies although the [100] projection of fcc structures, depicted in (b), is also observed over very small areas on rare occasions.

Example 8. Inventive Films from Concentrated Compositions Containing Hybrid Nanoparticles Self-assembled superlattices of Au NPs were formed by slow evaporation of concentrated hexanes dispersions (5 mg mL$^{-1}$) of NPs on diethylene glycol. Superlattices of Au NPs with different generations of dendron coating were investigated. In FIG. 7a, a self-assembled superlattice film of Au@DDT showing regions containing monolayer, bilayer, and trilayer is shown. Large area superlattices, shown for Au@G1 hybrids in FIG. 7b, were obtained for inventive NPs with dendritic ligands. These solids have much lower inorganic density than the Au@DDT superlattices, demonstrated in FIG. 7c, which shows a bilayer region of Au@G2. At high magnification, such as the Au@G4 superlattice shown in FIG. 7d, the dramatically larger interparticle distances (~12 nm) in the superlattice with dendron ligands become apparent. Typically, in all cases, the Au NP superlattices form close-packed hcp (hexagonal close-packed) assemblies, small regions of fcc arrangements (i.e. ABC stacks) were nevertheless sparingly found over very small areas, as shown in FIG. 8. Although these hybrids have a "soft" corona, the formation of close-packed superlattices as shown in FIG. 7 is still consistent with a model of entropy-driven crystallization of hard spheres, as the inventive hybrid nanoparticles are a priori spherical building blocks that occupy the highest possible volume fraction. Because the contribution of the ligand shell to the volume of the building block increases with the generation of ligand, the inorganic density of the close-packed superlattices decreases.

Figure 9:
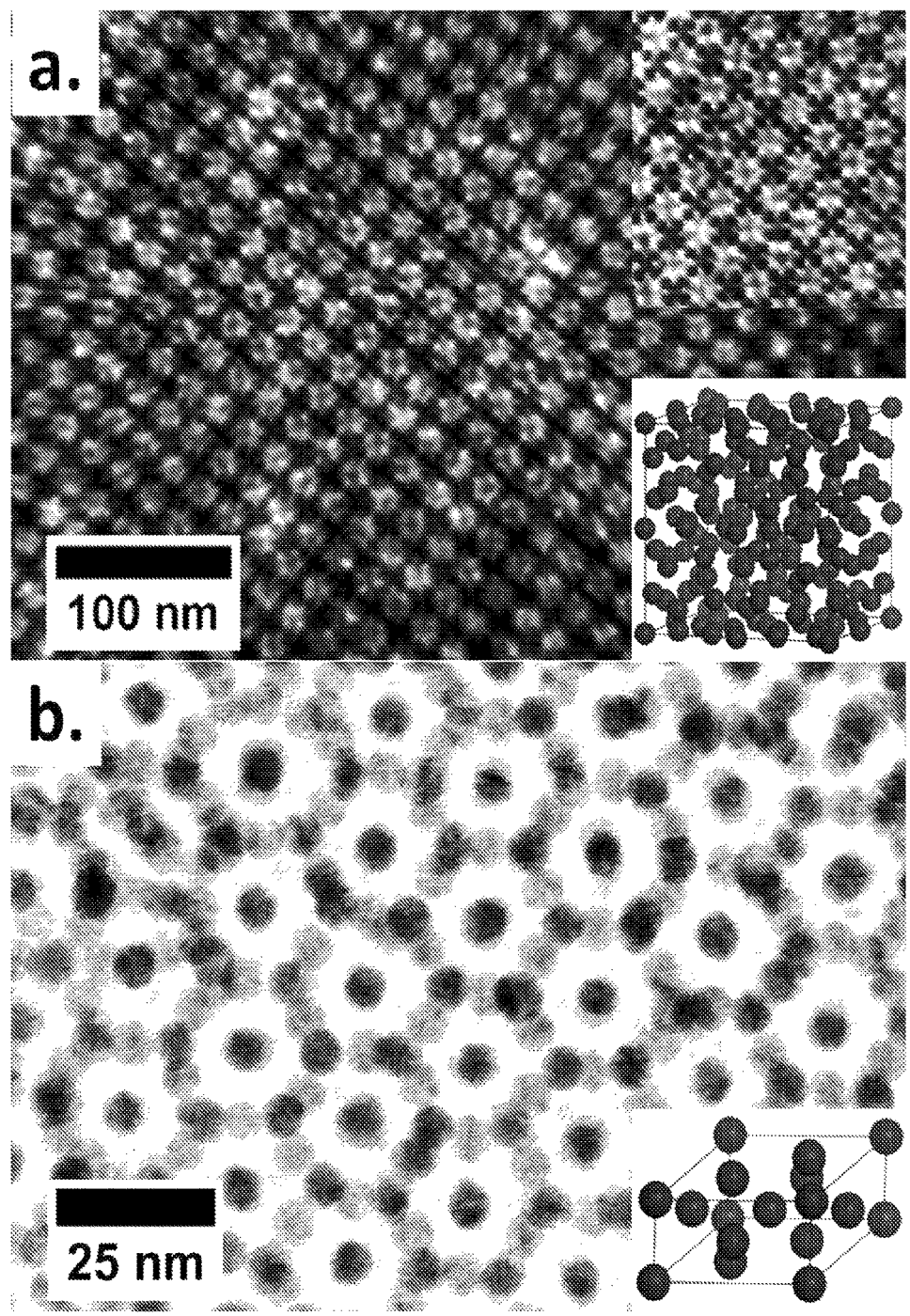
FIG. 9a shows a TEM micrograph of [100] zone axis of a cubic NaZn$_{13}$ superlattice comprised of Au@DDT and Au@G2 blends. Inset upper right is a thinner region of the sample. Inset lower right is a diagram of the unit cell (a≈42 nm), which contains 112 Au NPs.
FIG. 9b shows a TEM micrograph of [001] zone axis of a CaCu$_5$ superlattice formed from a mixture of Au@G1 and Au@G4 hybrids. Inset lower right is a drawing of the unit cell, which contains six Au NPs.

Example 9. Combination of Inventive Hybrid Nanoparticles of Different Effective Diameters The inventive hybrid nanoparticles described herein allow access to more complex self-assembled structures of a single inorganic building block by combining hybrid nanoparticles with different effective diameters (i.e. with different generation coatings): two superlattice structures of the $AB_{13}$ and $AB_5$ types, respectively, are shown in FIG. 9.

By mixing the monodisperse Au@DDT and Au@G2 hybrids, the effective diameter of the individual building blocks is adjusted to obtain a solid phase isostructural with the binary compound $NaZn_{13}$ (see FIG. 9a).

In the $NaZn_{13}$ structure, the Au@G2 hybrids, with an effective diameter ($\Phi_{hyb}$, Table 1) of 10.8 nm act as the larger spheres forming a simple cubic sublattice. Au@DDT hybrids, with an effective diameter of 8.2 nm form slightly distorted icosohedra in the interstices of the simple cubic lattice. Slight polydispersity is known to increase the space-filling of this structure, but at the diameter ratio of the Au@L samples used here ($\gamma \approx 0.76$), $NaZn_{13}$ structures show space filling of 59%, substantially less than single-component materials and other possible quasi-binary structures. Indeed, $NaZn_{13}$ structures were observed to co-exist with single-component superlattices of Au@DDT particles.

Mixing Au@G1 and Au@G4 hybrids, which have closer relative diameters, yields regions of a phase isostructural with $CaCu_5$ (see FIG. 9b).

To obtain the observed $CaCu_5$ structure, Au@G4 hybrids, with an effective diameter of 12.2 nm, act as the larger spheres, and Au@G1 hybrids, with an effective diameter of 10.2 nm, act as the smaller spheres. Space filling is an incomplete explanation for the observed $CaCu_5$ phase, which is less dense (62% at the size ratio of 0.84% used here) than single-component assemblies or other potential quasi-binary structures (e.g. CuAu).

Both of these crystal structures are known in binary elemental and colloidal systems (see, for example, Chen, Z.; Moore, J.; Radtke, G.; Sirringhaus, H.; O'Brien S. *J. Am. Chem. Soc.* 2007, 129, 15702). However, such crystal structures are not formed in other single-component assemblies.

Simple hard sphere models fail to explain the formation of nominally poorer space-filling $NaZn_{13}$ and $CaCu_5$ structures made by the inventive Au@L hybrid nanoparticles described herein. It can be seen that the inventive Au@L hybrid nanoparticles described herein are, on close inspection, neither hard nor spherical. Without wishing to be bound by theory, it is believed that the large organic volume fractions, as described herein, allow deformation of the spherical coronae of particles into Voronoï polyhedra that allow maximum space filling.

Lipophilic, highly flexible dendritic ligands of several generations tethered to the surface of NPs, particularly gold NPs, can control their spacing and their assemblies in the solid state. By changing the dendritic generation grafted on the particle surface, systematic tuning of the interparticle distances between Au NPs over a range intermediate between that of DNA-stabilized particles and spacings available with commercial reagents may be achieved, therefore providing an additional tool to engineer interparticle spacing in films and nanocomposites. The differentiation of the Au NP species with different dendrons was used to generate unprecedented complex single-component NP superlattices, which opens new frontiers in the field of NPs assemblies. Indeed, this important last result is very promising and motivates the exploration of many more binary combinations of hybrid nanoparticles having dendrons, considering various dendritic coatings and expanding the range of inorganic cores to different chemical compositions and shapes, to fabricate more exotic and functional multicomponent superlattices i.e. metamaterials with modulable and enhanced properties.

Example 10. Synthesis and Characterization of Large Hybrid Nanoparticles

Figure 10:
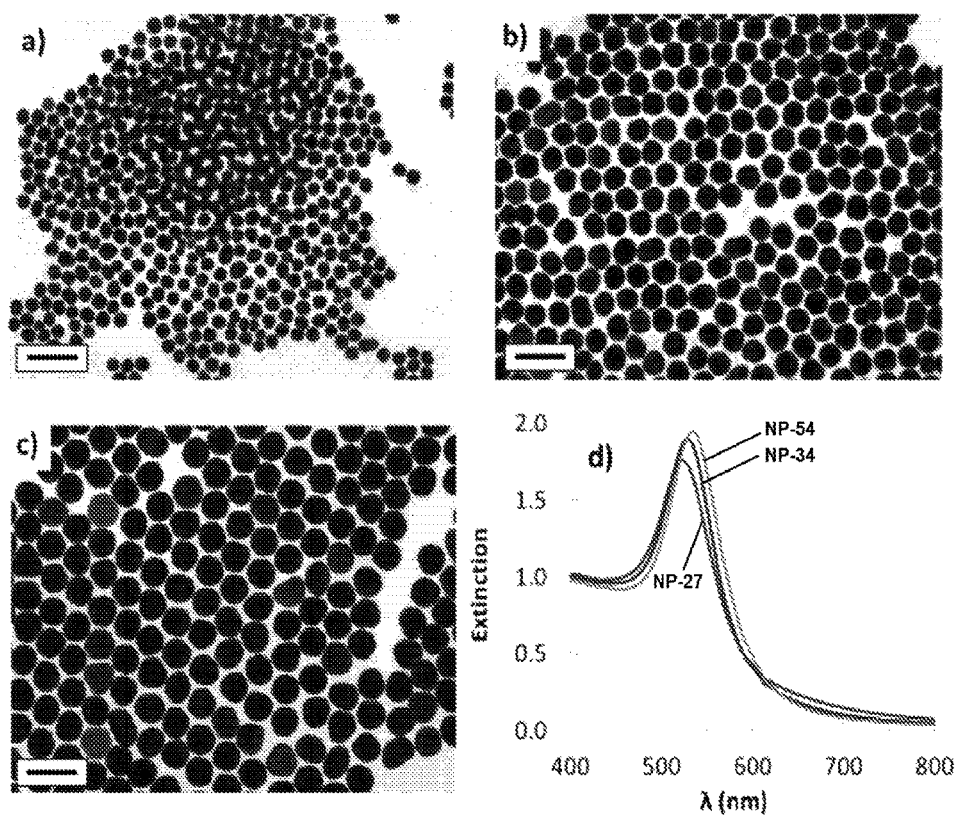
FIG. 10 shows TEM images (scale bar=50 nm) of Au@CTAB NPs as synthesized a) NP-27 b) NP-43 c) NP-54, and d) superposition of the corresponding extinction spectra (normalized at 400 nm).

Synthesis of gold nanoparticles, capped with cetyltrimethylammonium bromide (CTAB), was performed according to a published procedure (see J. Rodríguez-Fernández, J. Pérez-Juste, F. J. García de Abajo and L. M. Liz-Marzán, *Langmuir*, 2006, 22, 7007-7010). A solution of ascorbic acid (AA) was injected into an aqueous solution of gold salt $HAuCl_4$ and CTAB at 35° C. under a vigorous stirring ([Au]=1 mM, [CTAB]=1.5 mM, [AA]=2 mM). This injection was quickly followed by the addition of gold seed previously prepared using the Turkevich method. The size of the particles was tuned by the amount of seed injected into the solution. Three batches with different sizes were prepared from a [Au]=1 mM suspension of 14 nm seeds: NP-27, NP-43 and NP-54 with a diameter ($\Phi$) of 27±3 nm, 43±2 nm and 54±3 nm, respectively; volumes added were 28, 8 and 5.5 mL, respectively. FIG. 10 shows the TEM image of CTAB-capped nanoparticles designated a) NP-27, b) NP-43 and c) NP-54, with d) superposition of the corresponding extinction spectra (normalized at 400 nm).

Ligand exchange of the CTAB-capped nanoparticles was performed using the G2 dendrimer (compound 18) described herein. The CTAB-capped nanoparticles were separated out from water by centrifugation and the supernatant solution was replaced by a solution of THF containing a large excess of compound 18 (about 25 times excess by considering that each thiol group on average occupies ca. 0.2 $nm^2$ on the surface of the spherical NPs). The colloidal mixture was then placed in an ultra-sound bath at 50° C. for 45 min. This method appears to be robust as well as reproducible to replace the CTAB bilayer with compound 18 without aggregating the particles. Once the surface modification was performed, the hybrid nanoparticles, designated Au@G2-SS, could be transferred in any solvent of choice such as THF, chloroform or toluene by simple centrifugation followed by a subsequent re-dispersion sequence.

Figure 11:
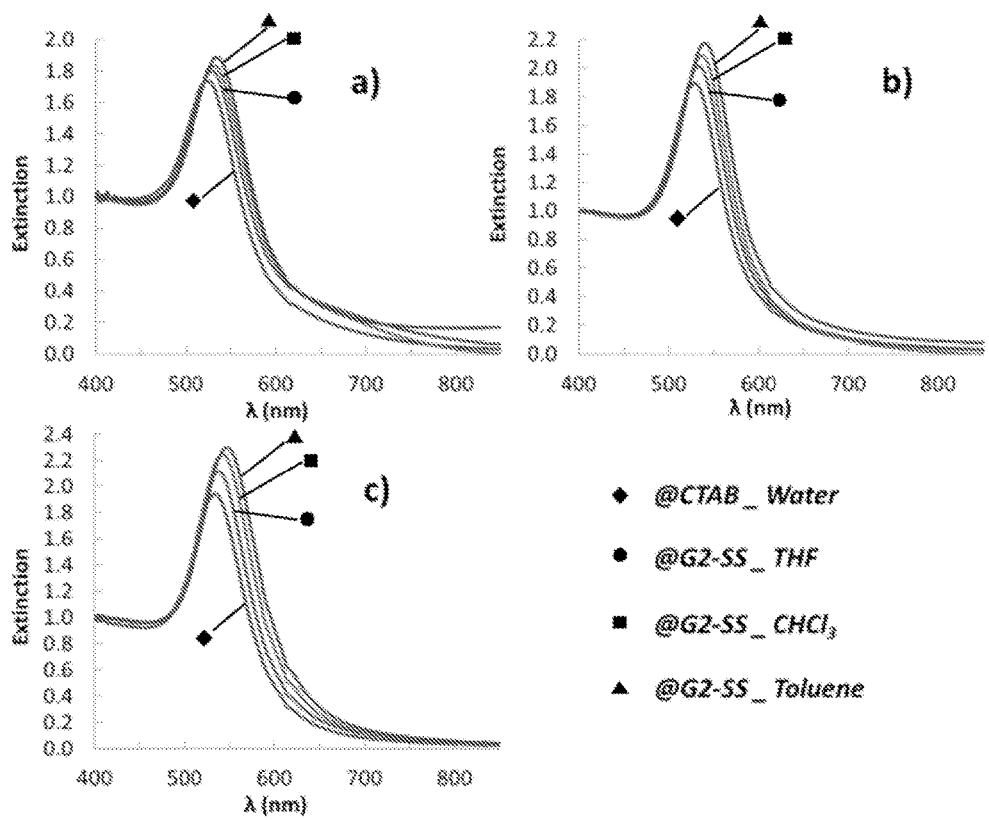
FIG. 11 shows extinction spectra (normalized at 400 nm) of a) NP-27 b) NP-43 and c) NP-54 in different solvents before (@CTAB_water) and after ligand exchange with G2-SS (compound 18).

The Au@G2-SS nanoparticles were characterized by UV/VIS spectroscopy and TEM. Extinction spectra were obtained for the three inventive samples in various solvents (e.g. THF, chloroform and toluene), including the extinction spectrum for the Au@CTAB nanoparticles in water for comparison. FIG. 11 shows the extinction spectra (normalized at 400 nm) of a) NP-27 b) NP-43 and c) NP-54 in the different solvents before and after ligand exchange with compound 18. The extinction spectra of the Au@G2-SS nanoparticles (i.e., after ligand exchange) did not show any broadening of the plasmon resonance peak when compared to that of the Au@CTAB nanoparticles (i.e., before ligand exchange). This result is indicative of well-dispersed and non-aggregated systems. Without wishing to be bound to theory, it is believed that the observed red-shift of the plasmon peak positions and intensity changes with different solvents are essentially due to the modification of the surrounding environment of the hybridized particles. As shown by FIG. 11 and Table 3 below, the higher the refractive index of the solvent, the larger the red-shift and the more intense the plasmon.

TABLE 3

Refractive indices at 20° C. of the different solvents used and plasmon maxima (nm) as a function of NP sizes and dispersing solvents.

|  | Water | THF | $CHCl_3$ | Toluene |
|---|---|---|---|---|
| n | 1.333 | 1.407 | 1.445 | 1.497 |
| $\lambda_{NP-27}$ | 524 | 529 | 533 | 536 |
| $\lambda_{NP-43}$ | 529 | 534 | 537 | 541 |
| $\lambda_{NP-54}$ | 534 | 538 | 543 | 547 |

Example 11. Formation of Ring Structure Comprising Hybrid Nanoparticles

Figure 12:
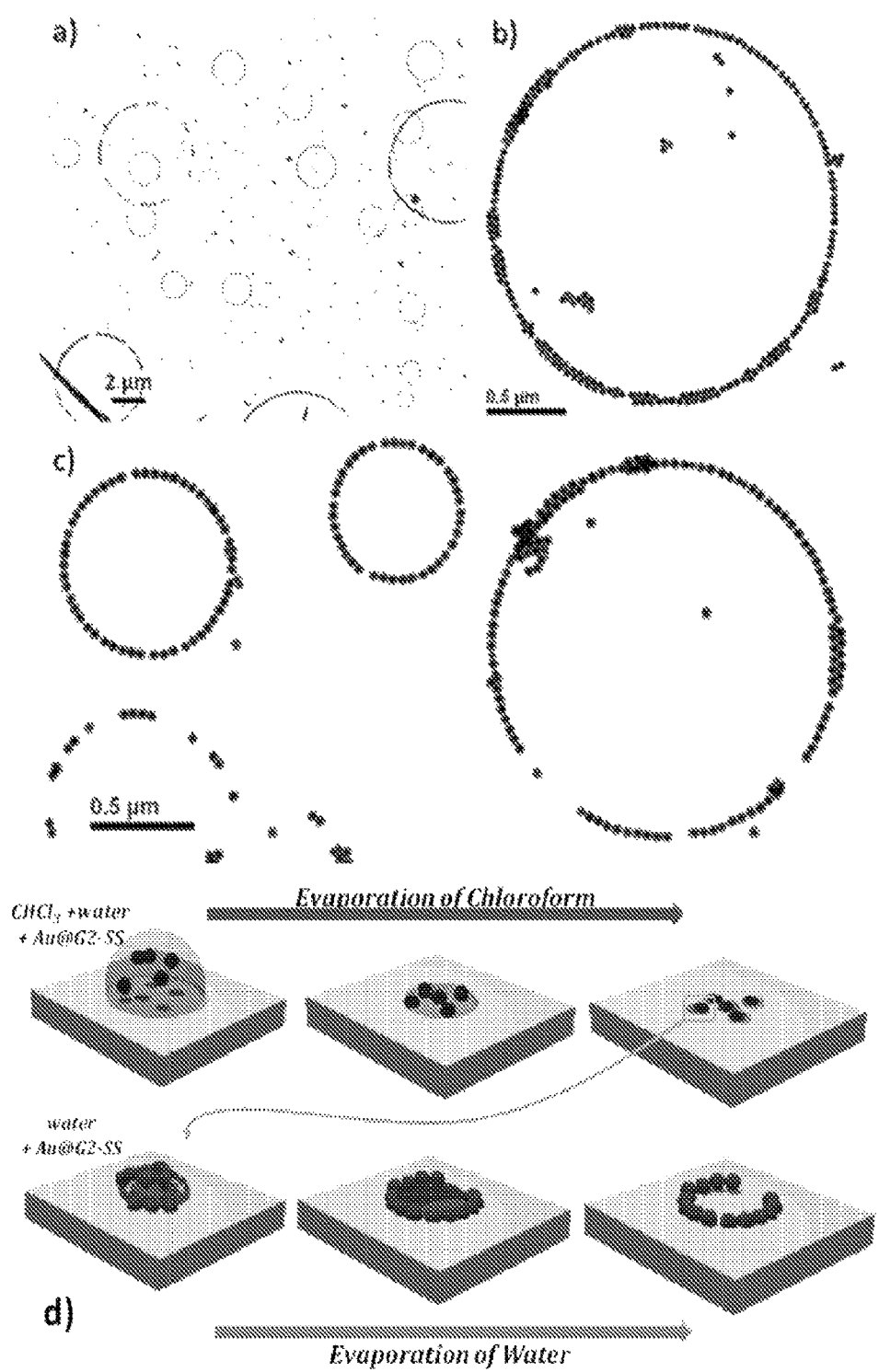
FIG. 12 shows TEM images of drop-casted NP-43@G2-SS in CHCl$_3$ with residual amounts of water at various magnification (scale bars: a) 2 μm, b & c) 500 nm).

When a solution of Au@G2-SS in chloroform was drop-casted just after its transfer from THF (with no additional rinse to remove residual traces of THF or water), the particles self-assemble as the solvent slowly evaporates to form perfect rings of various diameters. The formation of these rings is another good indication that the inventive hybrid nanoparticles are no longer water soluble. Without wishing to be bound by theory, it is believed that water, being immiscible with chloroform, first phase separates from the solvent in the form of perfectly circular micro-droplets due to the minimization of the surface tension at the water/solvent interface. The Au@G2-SS nanoparticles, being heavy and hydrophobic, then spontaneously self-assemble at the edges of the droplet, i.e. they are attracted and trapped at the interface of both liquids, thus forming the ring structures. The interface is actually a triple boundary (water/solvent/substrate) so while the entropy of the system is minimized at this interface, the potential energy of the system is on the contrary maximized, thus attracting the nanoparticles. When chloroform and THF first evaporate, stable rings of NPs are left behind all over the support. FIG. 12a to FIG. 12c show TEM images of the ring structures formed by the NP-43@G2-SS hybrid particles and FIG. 12d shows a possible mechanism by which the ring structures may be formed.

Deposition of Au@G2-SS dispersed in chloroform solutions onto solid substrates leads, upon slow solvent-evaporation, to their assembly into perfect nanoparticular rings, of all sizes (from a few nm to several μm), consequent to residual traces of water in the solvent. This opens many new perspectives to direct assemblies of very large nanoparticles of interest for various applications.

Figure 13:
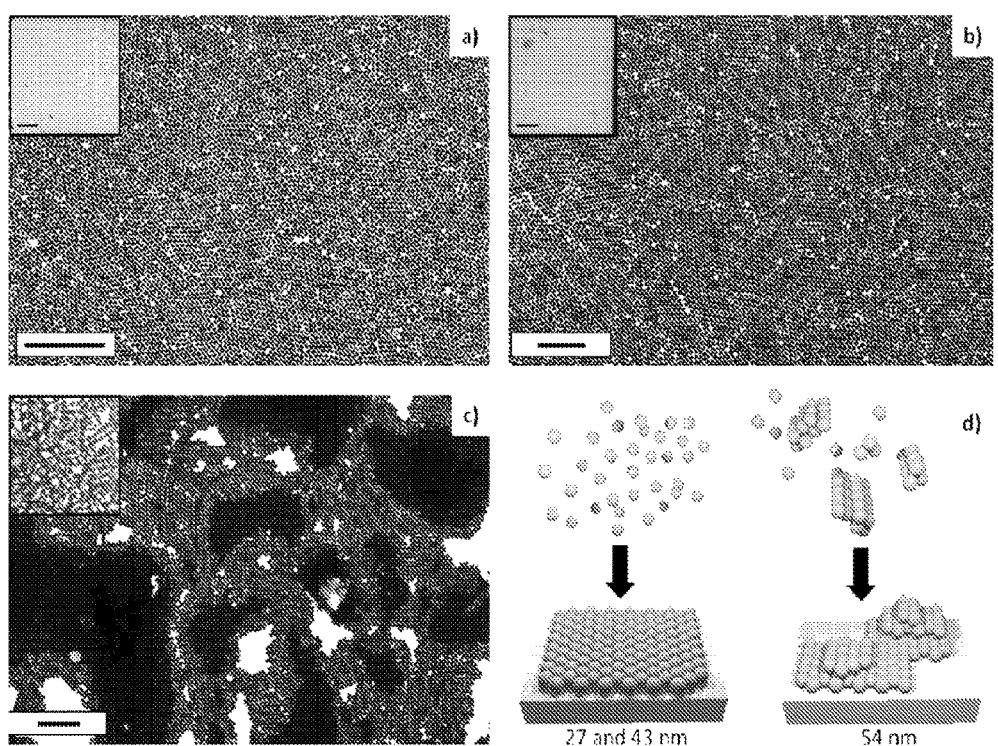
FIG. 13 shows TEM images of the monolayers obtained via slow evaporation of the inventive hybrid nanoparticles onto diethylene glycol subphase: a) NP-27@G2-SS, b) NP-43@G2-SS and c) NP-54@G2-SSnm. Scale bar=500 nm. The inset in each figure is a lower magnification of the corresponding film—Scale bar: 20 μm.

Example 12. Inventive Films from Compositions Containing Large Hybrid Nanoparticles Self-assembled monolayers were obtained by slow evaporation of concentrated toluene solutions of dispersed inventive hybrid nanoparticles ([Au]≈40 mM) on diethylene glycol. FIG. 13 shows TEM images of the monolayers obtained via slow evaporation of the inventive hybrid nanoparticles onto diethylene glycol subphase: a) NP-27@G2-SS, b) NP-43@G2-SS and c) NP-54@G2-SS. Bar scale is 500 nm. The inset in each figure is a lower magnification of the corresponding film, the bar scale being 20 μm. FIG. 13d shows a schematic of the transition from suspension to monolayers for the variously-sized nanoparticles.

As shown in FIG. 13, the NP-27@G2-SS and NP-43@G2-SS hybrids form uniform monolayers with extended semi-crystalline domains, with regularly hexagonally packed nanoparticles, over large areas (several tens of μm$^2$). In contrast, the larger particles, NP-54@G2-SS, form islands of multilayered systems, i.e. closed packed assemblies of hcp/fcc arrangements, perhaps an indication of their lower stability. It is worth highlighting that in our experiments, these large nanoparticles showed lower stability in concentrated suspensions than the other two sizes of nanoparticles. Upon concentration, it was observed that the corresponding suspension of NP-54@G2-SS turns violet, indicating some degree of aggregation. Without wishing to be bound by theory, such behaviour can be attributed a priori to their size and can be directly correlated with the DLVO theory. As the attractive interactions increase with the size of the particles (surrounded by the same organic shell), they become predominant and counterbalance the electrostatic repulsion for NP-54@G2-SS nanoparticles leading to some degrees of aggregation, while the repulsion forces still govern the suspension behaviour for the NP-27@G2-SS and NP-43@G2-SS particles. During the self-assembly via slow evaporation, NP-27@G2-SS and NP-43@G2-SS hybrids organize themselves into well-organized monolayer, whereas in case of the NP-54@G2-SS, the formation of 3D clusters may start (due to the concentration increase) before the formation of a 2D layer as solvent evaporates.

Figure 15:
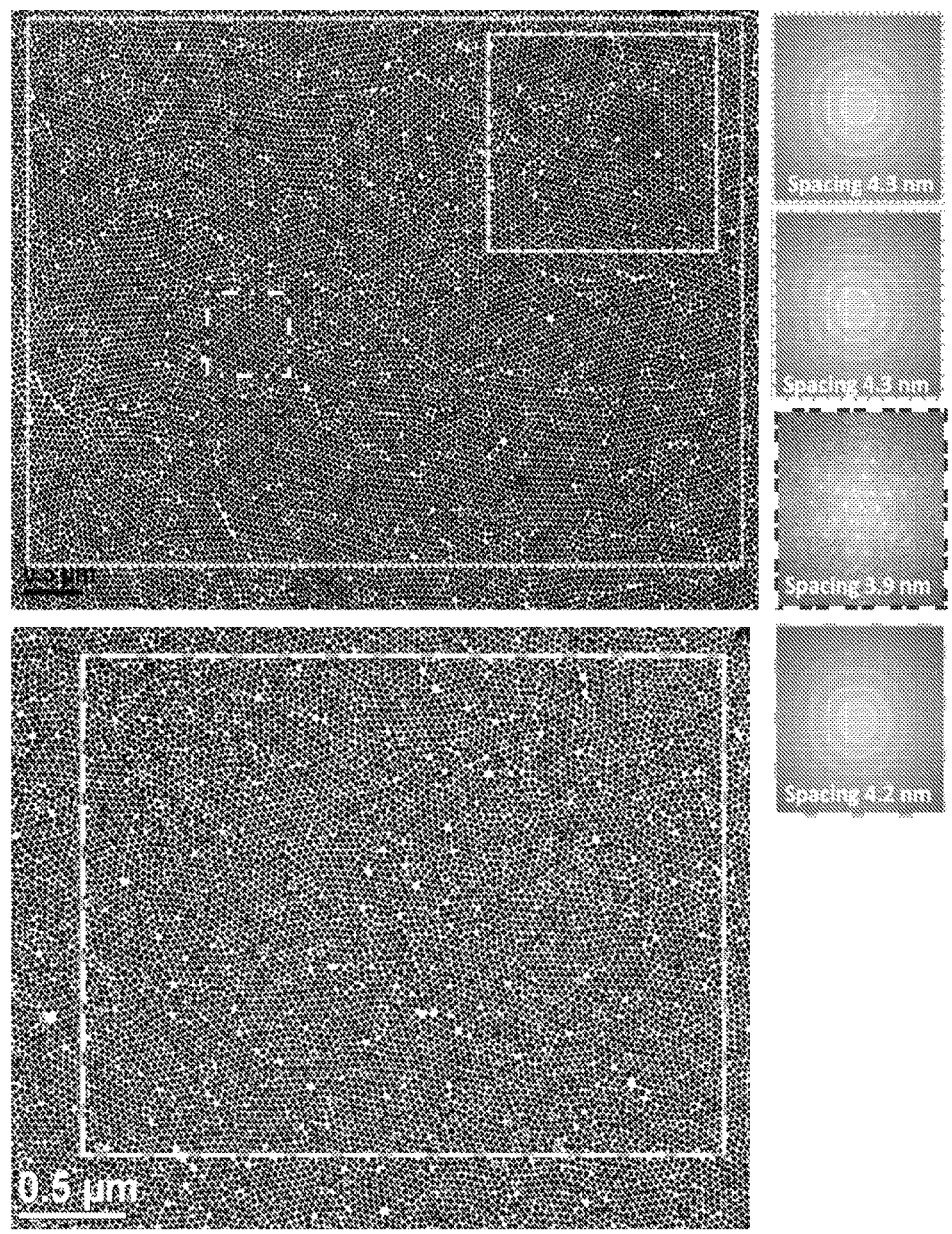
FIG. 15 shows the TEM images and the selected frames used for the Fast Fourier Transform analyses described herein.

FIG. 15 shows TEM images and the selected frames used for Fast Fourier Transform analyses. Fast Fourier Transform analyses of selected frames within these images reveal several order of diffraction, confirming the hexagonal lattice packing and the good quality of the arrangement of the nanoparticles. Calculations of the spacings lead to interparticle distances, a, of 31±1, 47±1 and 58±1 nm for NP-27@G2-SS, NP-43@G2-SS and NP-54@G2-SS respectively, which gives a separation between nanoparticles of about 4-4.5 nm.

Figure 14:
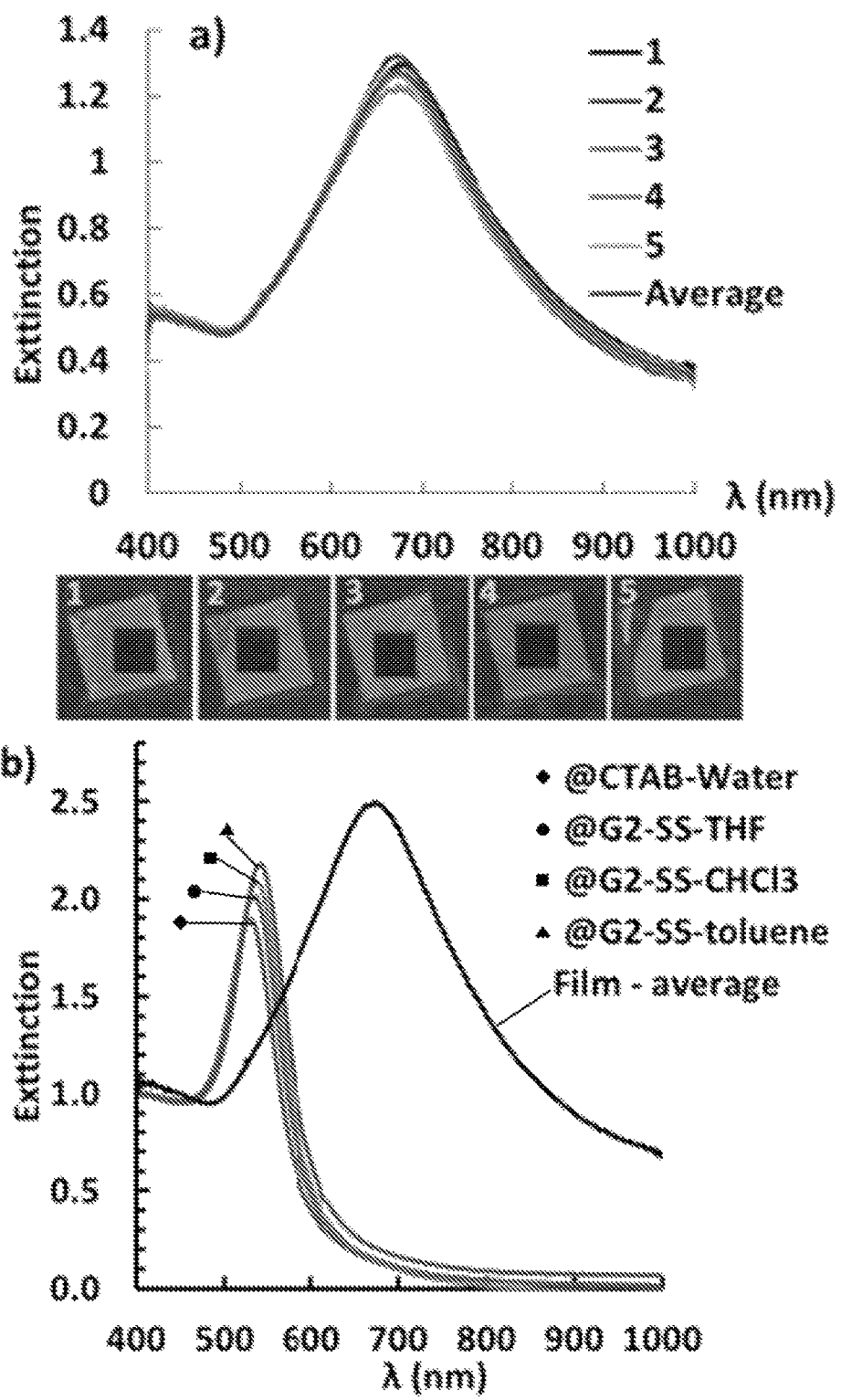
FIG. 14a shows extinction spectra of different zones on the films made of NP-45@G2-SS and the corresponding microscopy images (The black square is the measurement window and has a size of 24×24 μm$^2$).
FIG. 14b shows a comparison of the extinction spectra of NP-45@G2-SS in suspension and organized into monolayer.

The monolayers made with NP-43@G2-SS were further optically characterized with a microscope spectrophotometer. The film homogeneity was tested by taking measurements in 5 different areas of the film. FIG. 14 shows a) the extinction spectra of different zones (numbered 1-5) on the films made of NP-45@G2-SS and the corresponding microscopy images (The black square is the measurement window and has a size of 24×24 μm$^2$) and b) the comparison of the extinction spectra of NP-45@G2-SS in suspension and organized into monolayer.

As shown in FIG. 14a, very similar extinction spectra in all cases were found, evidencing that the film is highly uniform over very large areas. As shown in FIG. 14b, the maximum of the film absorption is red-shifted by 140 nm compared to the solution absorption spectrum, which is a clear indication of inter-particle plasmonic coupling that arises when particles are in close proximity.

The hybrid nanoparticles of the present disclosure are conveniently and efficiently dispersed in nonpolar solvents, such as, for example, toluene, which is a key parameter for the formation of monolayers at liquid-air interfaces, on very large areas and of high uniformity.

What is claimed is:
1. A hybrid nanoparticle comprising:
(a) a metallic core, and
(b) at least one dendron attached to the surface of the metallic core;
  wherein the at least one dendron is a lipophilic dendron, wherein the lipophilic dendron comprises one or more capping groups comprising an alkyl group having at least 6 carbon atoms.

2. The hybrid nanoparticle according to claim 1, wherein the metallic core comprises a transition metal.

3. The hybrid nanoparticle according to claim 1, wherein the metallic core comprises gold.

4. The hybrid nanoparticle according to claim 1, wherein the at least one dendron attached to the surface of the metallic core comprises the structure of formula (I) or (II):

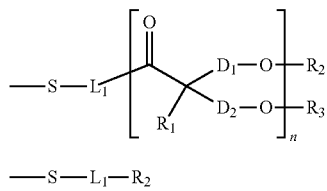

(I)

—S—L$_1$—R$_2$ (II)

wherein each occurrence of R$_1$ is H or C$_1$-C$_{20}$ alkyl, each occurrence of D$_1$ and D$_2$ are each, independently, C$_1$-C$_{20}$ alkylene, each occurrence of L$_1$ is C$_1$-C$_{20}$ alkylene, each occurrence R$_2$ and R$_3$ are each, independently, C$_6$-C$_{38}$ alkyl, n is from 1 to 6;

wherein R$_1$, D$_1$, and D$_2$, L$_1$, R$_2$, and R$_3$, are each optionally interrupted by one or more divalent moieties;

and is attached to the metallic core via the sulfur atom.

5. The hybrid nanoparticle according to claim 4, wherein n is from 1 to 4.

6. The hybrid nanoparticle according to claim 4, wherein R$_1$ is methyl.

7. The hybrid nanoparticle according to claim 4, wherein D$_1$ and D$_2$ are each methylene.

8. The hybrid nanoparticle according to claim 4, wherein R$_2$ and R$_3$ are each C$_{17}$-alkyl interrupted by

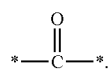

9. The hybrid nanoparticle according to claim 4, wherein L$_1$ is C$_{12}$-alkylene interrupted by —O— and

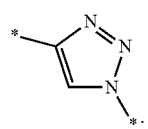

10. A film comprising a plurality of hybrid nanoparticles according to claim 1.

11. The film according to claim 10, wherein the interparticle distance between the hybrid nanoparticles is from about 9 nm to about 15 nm.

12. The film according to claim 10, wherein edge-to-edge separation between the hybrid nanoparticles is from about 3 nm to about 10 nm.

13. A dendrimer represented by the structure of formula (III) or (IV):

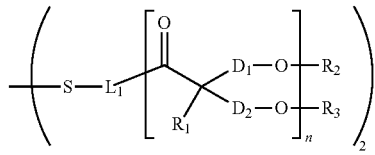

(III)

—(S—L$_1$—R$_2$)$_2$ (IV)

wherein each occurrence of R$_1$ is H or C$_1$-C$_{20}$ alkyl, each occurrence of D$_1$ and D$_2$ are each, independently, C$_1$-C$_{20}$ alkylene, each occurrence of L$_1$ is C$_1$-C$_{20}$ alkylene, each occurrence R$_2$ and R$_3$ are each, independently, C$_1$-C$_{38}$ alkyl, C$_2$-C$_{38}$ alkenyl, or C$_2$-C$_{38}$ alkynyl, n is from 1 to 6;

wherein R$_1$, D$_1$, and D$_2$, L$_1$, R$_2$, and R$_3$, are each optionally interrupted by one or more divalent moieties defined herein.

14. A method for producing the dendrimer according to claim 13, the method comprising:

reacting a compound represented by the structure of formula (V):

G$_1$-S—S-G$_1$ (V)

with a compound represented by the structure of formula (VI) or (VII):

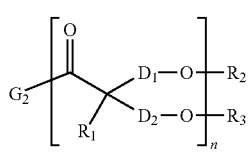

(VI)

G$_2$—R$_2$ (VII)

wherein each occurrence of R$_1$ is H or C$_1$-C$_{20}$ alkyl, each occurrence of D$_1$ and D$_2$ are each, independently, C$_1$-C$_{20}$ alkylene, each occurrence R$_2$ and R$_3$ are each, independently, C$_1$-C$_{38}$ alkyl, C$_2$-C$_{38}$ alkenyl, or C$_2$-C$_{38}$ alkynyl, n is from 1 to 6;

wherein R$_1$, D$_1$, and D$_2$, R$_2$, and R$_3$, are each optionally interrupted by one or more divalent moieties defined herein;

each occurrence of G$_1$ is a substituent comprising a reactive group capable of reacting with the reactive group in G$_2$, and G$_2$ is a substituent comprising a reactive group capable of reacting with the reactive group in G$_1$.

15. A method for producing the hybrid nanoparticle according to claim 1, the method comprising:

(i) producing the dendrimer represented by the structure of formula (III) or (IV):

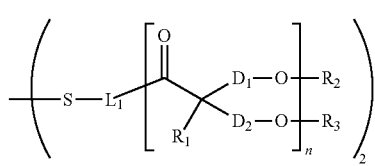

(III)

-continued

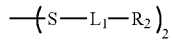
(IV)

wherein
each occurrence of $R_1$ is H or $C_1$-$C_{20}$ alkyl,
each occurrence of $D_1$ and $D_2$ are each, independently, $C_1$-$C_{20}$ alkylene,
each occurrence of $L_1$ is $C_1$-$C_{20}$ alkylene,
each occurrence $R_2$ and $R_3$ are each, independently, $C_6$-$C_{38}$ alkyl,
n is from 1 to 6;
wherein $R_1$, $D_1$, and $D_2$, $L_1$, $R_2$, and $R_3$, are each optionally interrupted by one or more divalent moieties, and
    (ii) contacting the dendrimer produced in step (i) with a metallic nanoparticle;
thereby producing the hybrid nanoparticle.

16. A composition comprising at least one hybrid nanoparticle according to claim 1 and a liquid carrier.

17. A composition according to claim 16, wherein the liquid carrier comprises hexane, or isomers thereof.

18. A method for producing the film according to claim 10, the method comprising:
    (i) coating a composition comprising at least one hybrid nanoparticle comprising:
      (a) a metallic core, and
      (b) at least one dendron attached to the surface of the metallic core;
        wherein the at least one dendron is a lipophilic dendron, wherein the lipophilic dendron comprises one or more capping groups comprising an alkyl group having at least 6 carbon atoms;
    and a liquid carrier,
on the surface of a liquid immiscible with the liquid carrier of the composition, and
    (ii) removing the liquid carrier of the composition, thereby producing the film.

19. A method for producing a ring structure comprising a plurality of hybrid nanoparticles, the method comprising:
    (i) coating a composition comprising hybrid nanoparticles according to claim 1, the liquid carrier of which comprises a residual amount of water, on the surface of a support, and
    (ii) removing the liquid carrier of the composition, thereby producing the ring structure.

* * * * *